US009695953B2

(12) United States Patent
Burnard et al.

(10) Patent No.: US 9,695,953 B2
(45) Date of Patent: Jul. 4, 2017

(54) NEEDLELESS ACCESS PORT VALVES

(75) Inventors: Edwin L. Burnard, Pen Argyl, PA (US); David M. Nelson, Allentown, PA (US)

(73) Assignee: B. Braun Medical Inc., Bethlehem, PA (US)

( * ) Notice: Subject to any disclaimer, the term of this patent is extended or adjusted under 35 U.S.C. 154(b) by 2469 days.

(21) Appl. No.: 12/510,937

(22) Filed: Jul. 28, 2009

(65) Prior Publication Data
US 2011/0024664 A1 Feb. 3, 2011

(51) Int. Cl.
*A61M 39/26* (2006.01)
*F16K 15/14* (2006.01)
*A61M 39/02* (2006.01)

(52) U.S. Cl.
CPC ........... *F16K 15/147* (2013.01); *A61M 39/26* (2013.01); *A61M 39/02* (2013.01); *A61M 2205/0222* (2013.01)

(58) Field of Classification Search
CPC .................. F16K 15/147; A61M 39/26; A61M 2205/0222; A61M 39/02
USPC ..... 251/149.1, 149.7, 149.6; 604/34, 167.04, 604/249, 256
See application file for complete search history.

(56) References Cited

U.S. PATENT DOCUMENTS

| 4,603,152 A | 7/1986 | Laurin et al. |
| 4,838,875 A | 6/1989 | Somor |
| 5,049,139 A | 9/1991 | Gilchrist |
| 5,354,267 A | 10/1994 | Niermann et al. |
| 5,439,451 A | 8/1995 | Collinson et al. |
| 5,536,258 A | 7/1996 | Folden |
| 5,547,000 A | 8/1996 | Kemp et al. |
| 5,549,577 A | 8/1996 | Siegel et al. |
| 5,699,821 A | 12/1997 | Paradis |
| 5,782,808 A | 7/1998 | Folden |
| 6,079,432 A | 6/2000 | Paradis |
| 6,448,306 B1 | 9/2002 | Lever et al. |
| 6,822,034 B2 | 11/2004 | Hanke et al. |
| 6,871,838 B2 * | 3/2005 | Raines et al. .............. 251/149.4 |
| 2002/0133124 A1 | 9/2002 | Leinsing et al. |
| 2003/0199835 A1 | 10/2003 | Leinsing et al. |
| 2004/0133171 A1 | 7/2004 | Newton et al. |

(Continued)

FOREIGN PATENT DOCUMENTS

WO    WO 00/59561    10/2000

OTHER PUBLICATIONS

PCT International Search Report completed Aug. 9, 2007 and mailed Oct. 1, 2007 from corresponding PCT U.S. Appl. No. PCT/US2007/00666, filed Jan. 10, 2007 (2 pages).

(Continued)

*Primary Examiner* — Craig Schneider
*Assistant Examiner* — Andrew J Rost
(74) *Attorney, Agent, or Firm* — Klein, O'Neill & Singh, LLP

(57) ABSTRACT

Needleless access port valves are generally discussed herein with particular discussions extended to needleless access port valves incorporating a piston comprising slit along an upper piston section for accommodating fluid flow. The slit opens when the piston is compressed by a medical implement, such as a syringe tip, to permit fluid communication between the inlet and the outlet of the vale housing. The slit may be cut using high frequency cutting machine or a multi-axis robot arm and a cutting blade.

20 Claims, 20 Drawing Sheets

(56) References Cited

U.S. PATENT DOCUMENTS

| | | |
|---|---|---|
| 2004/0166163 A1 | 8/2004 | Kimura et al. |
| 2004/0195538 A1 | 10/2004 | Raines et al. |
| 2004/0234572 A1 | 11/2004 | Martinod et al. |
| 2006/0163515 A1 | 7/2006 | Ruschke |
| 2006/0293629 A1 | 12/2006 | Cote, Sr. et al. |
| 2007/0191786 A1 | 8/2007 | Raines et al. |
| 2007/0270756 A1 | 11/2007 | Peppel et al. |
| 2009/0184275 A1 | 7/2009 | Ruschke et al. |

OTHER PUBLICATIONS

PCT Written Opinion completed Aug. 9, 2007 and mailed Oct. 1, 2007 from corresponding PCT U.S. Appl. No. PCT/US2007/00666, filed Jan. 10, 2007 (5 pages).

Preliminary Report on Patentability (Chapter 1 of the Patent Cooperation Treaty) from corresponding PCT U.S. Appl. No. PCT/US2007/00666, filed Jan. 10, 2007 (7 pages).

Office Action mailed Sep. 29, 2008 from corresponding U.S. Appl. No. 11/354,345, filed Feb. 14, 2006.

Office Action mailed Dec. 23, 2008 from corresponding U.S. Appl. No. 11/354,345, filed Feb. 14, 2006.

Notice of Allowance mailed May 19, 2009 from corresponding U.S. Appl. No. 11/354,345, filed Feb. 14, 2006.

PCT International Search Report completed May 14, 2008 and mailed Jun. 25, 2008 from corresponding PCT U.S. Appl. No. PCT/US2007/085130, filed Nov. 19, 2007 (3 pages).

PCT Written Opinion May 14, 2008 and mailed Jun. 25, 2008 from corresponding PCT U.S. Appl. No. PCT/US2007/085130, filed Nov. 19, 2007 (6 pages).

PCT International Search Report completed Jan. 24, 2011 and mailed Jan. 25, 2011 from corresponding PCT Application No. US2010-039849, filed Jun. 24, 2010 (3 pages).

PCT Written Opinion completed Jan. 24, 2011 and mailed Jan. 25, 2011 from corresponding PCT U.S. Appl. No. US2010-039849. filed Jun. 24, 2010 (5 pages).

Preliminary Report on Patentability completed Jan. 31, 2012 and mailed Feb. 9, 2012 from corresponding International Application No. PCT/US2010/039849 filed Jun. 24, 2010 (8 pages).

Examiner's Report on corresponding foreign application (AU Application No. 2010281604) from the Australian Intellectual Property Office dated Oct. 21, 2015.

\* cited by examiner

NEEDLELESS ACCESS PORT VALVES

CROSS-REFERENCE TO RELATED APPLICATION(s)

This application may be related to Ser. No. 11/354,345, filed Feb. 14, 2006, and to Ser. No. 11/942,163, filed Nov. 19, 2007. The contents of the identified two applications are expressly incorporated herein by reference for all purposes.

TECHNICAL FIELD

The present invention is related to needleless access port valves, and more particularly to needleless access port valves having a movable piston for creating a fluid flow path between an inlet and an outlet of a valve housing. In certain embodiments, the piston incorporates a slit of different configurations to permit fluid flow between the piston and an interior surface of the housing.

BACKGROUND

Needleless access port valves are widely used in the medical industry for accessing an IV line and/or the internals of a patient or subject. Commonly, a valve housing in combination with a moveable internal plug or piston is used to control the flow of fluid through the needleless valve. The plug or piston may be moved by a syringe or a medical implement to open the inlet of the valve for accessing the interior cavity of the valve. When a fluid is delivered through the valve, fluid flow typically flows around the outside of the plug or piston in the direction towards the outlet. Upon removal of the syringe or medical implement, the plug or piston returns to its original position, either un-aided or aided by a biasing means, such as a spring or a diaphragm.

In some valves, when the syringe or medical implement pushes the plug or piston, the plug or piston is pierced by an internal piercing device, such as a spike. The spike typically incorporates one or more fluid channels for fluid flow flowing through the pierced piston and then through the fluid channels in the spike. In yet other prior art valves, a self-flushing or positive flush feature is incorporated to push residual fluids confined inside the interior cavity of the valve to flow out the outlet when the syringe or medical implement is removed.

While prior art needleless access port valves are viable options for their intended applications, there remains a need for alternative needleless access port valves.

SUMMARY

The present invention may be implemented by providing a valve assembly comprising: a valve housing having an interior cavity, a bottom opening, and an inlet nozzle having an inlet opening and an interior wall surface along a central axis; a piston positioned inside the valve housing having a flange, a neck section, a body section, and a base; the piston further comprising a slit having a first slit surface and a second slit surface extending radially across two opposed exterior surface sections of the flange and lengthwise in a direction of the inlet opening towards the bottom opening and through at least part of the neck section below the flange, the first slit surface and second slit surface extending through at least part of the neck section below the flange and comprises an angle about the central axis.

The present invention may also be practiced by providing a valve assembly comprising: a piston positioned inside a valve housing, the piston comprising a flange, a neck section, a body section comprising an upper section and a lower section defining an interior cavity, an exterior wall surface, and a base; the valve housing comprising an inlet nozzle having an inlet opening, a body section defining an interior cavity having an interior wall surface, and a bottom opening; wherein the neck section of the piston comprises a slit formed across the entire flange and through at least part of the neck section to the exterior wall surface of the piston in a helical configuration; the slit defining a fluid space with the interior wall surface of the valve housing for fluid flow through the inlet nozzle and out the bottom opening.

The present invention further includes a method of making a piston for use in an access port valve, said method comprising: molding a piston, said piston comprising a neck section of reduced diameter compared to a body section, which defines an interior cavity; and cutting a slit in the neck section; wherein the cutting step comprises rotating a blade by an angle about an axis of the piston while translating the blade by a distance along the axis.

Aspects of the present invention further include provisions for an actuator co-molded with the piston for opening a slit.

Still other aspects of the present invention includes incorporating internal indentations and/or ribs for creating fluid flow paths inside the interior cavity of a valve housing.

The present invention includes provisions for incorporating antimicrobial agents into at least one of a piston, a valve housing, and a nut fitting for controlling unwanted microbial growth. Exemplary agents include silver, gold, copper and their compounds.

A still further aspect of the present invention includes the provision for cutting a slit on a piston through a cutting process. Exemplary processes include thin blade cutting, cutting by laser, by water jet cutting, and with a combination blade and ultrasonic generator device.

These and other features and advantages of the present invention will become appreciated as the same become better understood with reference to the specification, claims and appended drawings.

BRIEF DESCRIPTION OF THE DRAWINGS

The drawings appended herein include.

DETAILED DESCRIPTION

The detailed description set forth below in connection with the appended drawings is intended as a description of various embodiments of needleless access port valves or backcheck valves (hereinafter "valves") provided in accordance with aspects of the present invention and is not intended to represent the only forms in which the present invention may be constructed or used. The description sets forth the features and the steps for constructing and using the valves of the present invention in connection with the illustrated embodiments. It is to be understood, however, that the same or equivalent functions and structures may be accomplished by different embodiments that are also intended to be encompassed within the spirit and scope of the invention. As denoted elsewhere herein like element numbers are intended to indicate like or similar elements or features.

Figure 1:
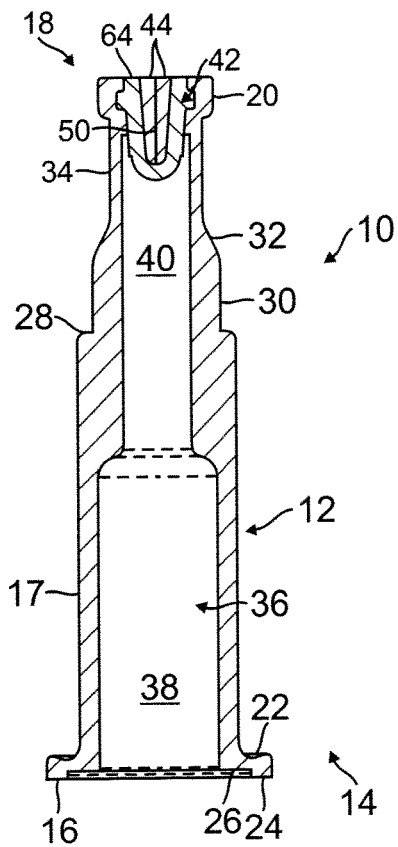
FIG. 1 is a semi-schematic cross-sectional side view of a valve piston provided in accordance with aspects of the present invention, which has an inlet actuator configured to open and close the upper section of the piston to create a fluid flow path.

Referring now to FIG. 1, a semi-schematic cross-sectional side view of a valve piston or piston provided in accordance with aspects of the present invention is shown, which is generally designated 10. As further discussed below, the piston 10 is configured to regulate flow through a valve housing by expanding and sealing against the valve housing to inhibit flow between the inlet and the outlet of the housing and compressing or deforming to permit flow between the two. In one exemplary embodiment, the piston 10 comprises a flexible elastomeric body 12 comprising a first end 14 comprising a base or first flange 16 and a second end 18 comprising a second flange 20. For purposes of discussion only, the first end 14 will be identified as a base end and the second end 18 will be identified as a regulating end.

As provided in accordance with aspects of the present invention, the first flange or base flange 16 has an external diameter larger than the diameter of the body section 17 of the piston body 12. The flange 16 upper surface 22, lower surface 24 and recessed lower surface 26 are configured to be compressed in between a nut fitting and a flange seat located on the valve housing as described in U.S. Pat. No. 6,871,838 (herein "the '838 patent"), its contents are hereby expressly incorporated herein by reference.

In one exemplary embodiment, the body section 17 of the piston body 12 comprises a generally straight cylindrical wall structure that extends between the base flange 16 and a first shoulder 28 with a slight taper, such as a draft angle, being acceptable. A lower neck section 30 extends proximally of the first shoulder 28 having a smaller diameter than the diameter of the body section 17. A reducer section 32 extends proximally of the lower neck section 30 (or enlarger section if viewed from a proximal direction to a distal direction) into the upper neck section 34, which connects with the upper flange 20. When the piston 10 is positioned inside a valve housing (not shown), the first shoulder 28 and the second flange 20 engage corresponding surfaces inside the interior cavity of the housing to restrict flow around the exterior surface of the piston, which is around the flow space defined by the interior surface of the valve housing and the exterior surface of the piston, as further discussed below.

The piston body 12 defines an interior cavity 36 having a lower cavity chamber 38 and an upper cavity chamber 40. In one exemplary embodiment, the interior cavity 36 is in fluid communication with ambient atmosphere. Thus, air moves in and out of the interior cavity 36 of the piston body 12 when the same is depressed and released.

In one exemplary embodiment, the piston 10 is made from a flexible elastomeric material with silicone being more preferred. Alternatively, the piston may be made from a thermoplastic elastomer (TPE) type, such as the copolyamide (COPA) family of thermoplastic elastomers. In an exemplary embodiment, the COPA is copolyamide thermoplastic elastomer having a commercial trade name PEBAX®. However, other TPEs may also be used including thermoplastic polyurethanes (TPUs), styrenic thermoplastic elastomers, thermoplastic polyolefins (TPOs), copolyesters (COPEs), and thermoplastic vulcanizate elastomeric alloys (TPVs). Optionally, the TPEs may be cross-linked either chemically or by irradiation to alter their characteristics. Still alternatively, the piston may be made from a self-lube silicone material as disclosed in the '838 patent. The piston 10 is preferably self-resilient in that it flexes when compressed and restores to substantially its original shape when a load or force applied on the piston is removed without aid of a spring However, like the '838 patent, which was previously incorporated by reference, a spring may be incorporated to facility recovery of the piston upon removal of the applied force. When an external biasing member is used to aid in the recovery of the piston from a second position to a less compressed first position, the piston body may be made from a pliable material but not necessary resilient material. Less compressed state is measured with respect to the body section, which is under less axial compression when in a first position as compared to the second position.

In one exemplary embodiment, antimicrobial compositions are provided for controlling or combating bacterial contamination inside a valve, such as reducing the amount of biofilm formation. Use of antimicrobial compositions in medical devices are well known in the art and are described in, for example, U.S. Pat. No. 4,603,152 to Laurin et al., U.S. Pat. No. 5,049,139 to Gilchrist, and U.S. Pat. No. 5,782,808 to Folden. Use of antimicrobial compositions are also disclosed in publication Nos. 2002/0133124 A1 and 2003/0199835 A1, both to Leinsing et al. The contents of these patents and publications are expressly incorporated herein by reference as if set forth in full. In one specific aspects of the present invention, silver zirconium phosphate is formulated into the molding material for molding the piston 10, i.e., added to the TPE, silicone, or self-lube silicone material. The silver compound may vary between about 4% to about 10% by weight of the blended injectant with a preferred range of between about 6% and about 8%. Alternatively or in addition thereto, antimicrobial compositions are blended in the materials for molding the valve housing and/or nut fitting, which are further discussed below. Other antimicrobial agents useable with the components of the present invention include: silver, gold, platinum, copper, and zinc. Antimicrobial metal compounds used herein include oxides and salts of preferably silver and also gold, for example: silver acetate, silver benzoate, silver carbonate, silver citrate, silver chloride, silver iodide, silver nitrate, silver oxide, silver sulfa diazine, silver sulfate, gold chloride and gold oxide. Platinum compounds such as chloroplatinic acid or its salts (e.g., sodium and calcium chloroplatinate) may also be used. Also, compounds of copper and zinc may be used, for example: oxides and salts of copper and zinc such as those indicated above for silver. Single physiological, antimicrobial metal compounds or combinations of physiological, antimicrobial metal compounds may be used. Still alternatively, a thin antimicrobial agent may be deposited over a wall surface of the various valve components as disclosed in the '808 Folden patent.

In one exemplary embodiment, the piston has the following physical properties: about 1.15 specific gravity with a range of about 1.1 to about 1.2 being acceptable; a 50 durometer Shore A with an acceptable range of about 40 to about 60 durometer; at least 600 psi minimum tensile strength with about 800 psi minimum being more preferred; an elongation rating of about 275% minimum with about 350% minimum being more preferred; and a tear strength of about 100 ppi (pounds per inch) minimum with 125 ppi being more preferred. These values are provided as exemplary properties of certain piston embodiments only and that for certain applications and material selections, the value may vary.

Figure 2:
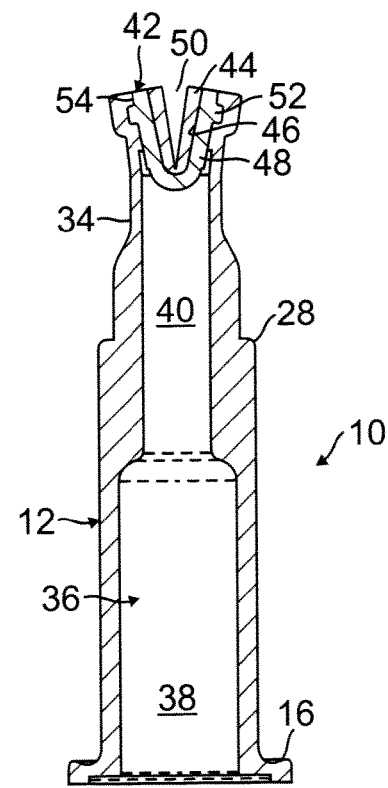
FIG. 2 is a semi-schematic cross-sectional side view of the valve piston of FIG. 1 with the inlet actuator in an open position.

In one exemplary embodiment, an inlet actuator 42 is incorporated on the upper neck section 34 of the piston body 12 for opening and closing a fluid pathway formed through the second flange 20 and at least part of the upper neck section 34. The inlet actuator 42 may be made from a rigid or semi-rigid thermoplastic, such as glass-filled nylon, and is molded to the piston body 12 using an over-molded process. The inlet actuator 42 has a generally V-shape configuration and has an inside surface 46 and an outside surface 48 (FIG. 2). Two opposing inlet plates 44 are formed on the inside surface 46 of the inlet actuator 42. A seam 50 is formed between the two inlet plates. In one exemplary embodiment, the two inlet plates 44 are made from the same material as the piston body 12 and are over-molded to the inlet actuator 42 and integral with the piston body. The inlet plates 44, being pliable, form a fluid tight seal along at least a portion of the seam 50 when the piston 10 is in the less compressed state with the two plates in contact with one another as shown in FIG. 1, which corresponds to a piston first position when positioned inside a valve housing. Preferably, the seam 50 is aligned along a lengthwise axis of the piston. However, the seam can extend transversely of the lengthwise axis of the piston without deviating from the spirit and scope of the present invention.

FIG. 2 is a semi-schematic cross-sectional side view of the piston 10 of FIG. 1 shown with the inlet actuator 42 in an open configuration. In one exemplary embodiment, the inlet actuator 42 naturally biases to the open position shown in FIG. 2 and the seam 50 separates when no force is applied to the outside surface 48 of the actuator 42 to form a gap. In one exemplary embodiment, a projection 52 on the outside surface 48 of the inlet actuator and a corresponding groove 52 on the interior surface of the upper neck section 34 are incorporated to enhance bonding or engagement between the inlet actuator and the piston body. However, multiple grooves and multiple projections, a reverse groove and projection configuration between the inlet actuator and the piston body, or a combination of both projections and grooves on the inlet actuator and the piston body may be incorporated without deviating from the spirit and scope of the present invention.

Figure 3:
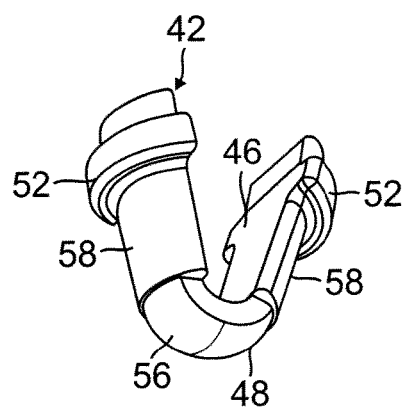
FIG. 3 is a semi-schematic perspective view of an actuator provided in accordance with aspects of the present invention.

FIG. 3 is a semi-schematic perspective view of an inlet actuator 42 provided in accordance with aspects of the present invention. In one exemplary embodiment, the inlet actuator 42 comprises an arc base 56 and two extension members 58 forming a V-shape structure with a more rounded apex at the arc base 56 than a typical V. The generally V-shape structure causes the two extensions 48 to diverge so that the two inside surfaces 46 do not normally touch or contact one another, i.e., are biased away from one another.

Figure 4:
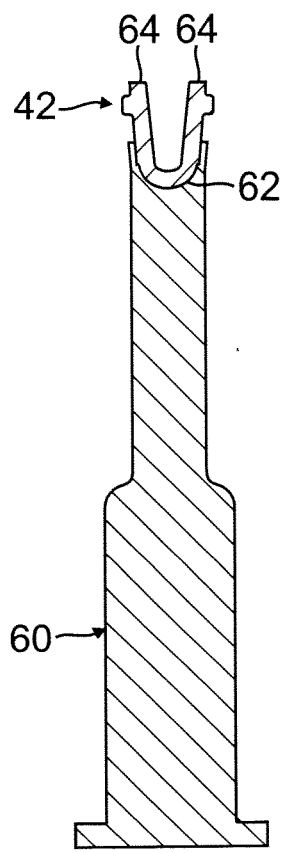
FIG. 4 is a semi-schematic cross-sectional side view of the actuator mounted on a core pin for forming the piston.

FIG. 4 is a semi-schematic cross-sectional side view of the inlet actuator 42 mounted on a core pin 60. The core pin 60 forms the contour of the interior cavity of the piston body 12 and is configured to work in conjunction with a mold and the inlet actuator 42 to form the piston 10. The core pin 60 includes a receptacle 62 for receiving and holding the inlet actuator 42 in a somewhat compressed state with the ends 64 of the two extensions 58 moved closer to one another than when in a normal expanded state shown in FIG. 3.

Figure 5:
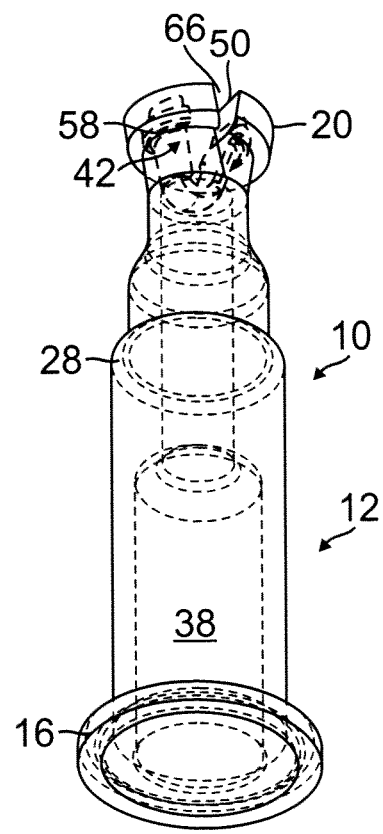
FIG. 5 is a semi-schematic perspective view of the piston of FIG. 1, which shows the actuator in an open position and various contours and hidden lines as dashed-dot lines.

FIG. 5 is a semi-schematic perspective view of the piston 10 of FIG. 2 shown with dot-dashed lines representing hidden lines. When no inwardly acting force is applied on the two extensions 58 of the inlet actuator 42 (i.e., when the extensions 58 are not constraint), they spread open to enlarge the seam 50 and create a gap 66. Hence, if fluid is placed at the ends 64 of the extensions 58, they will flow in between and out through the side gaps 66 of the seam 50.

Figure 6:
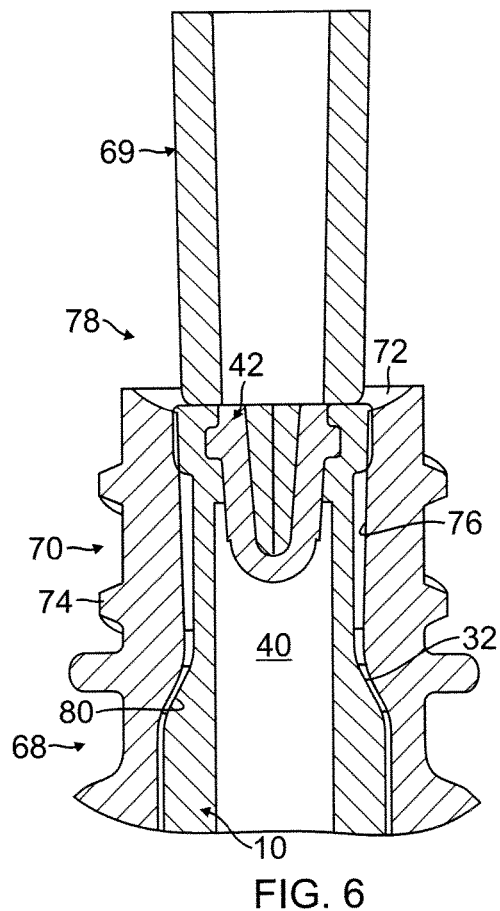
FIG. 6 is a semi-schematic partial cross-sectional side view of the piston of FIG. 1 positioned inside a valve housing in a first closed position and with a partial view of a tip of a medical implement.

FIG. 6 is a partial semi-schematic side-view of the piston 10 of FIG. 1 positioned inside a valve housing 68 in a closed or first position shown with a tip 69 of a medical implement, such as a syringe or a tubing adaptor. The valve housing 68 comprises an inlet nozzle 70 defining an inlet opening 72. In one exemplary embodiment, the inlet comprises a Luer inlet, which comprises external threads 74 but may have no threads, i.e., a Luer slip. The interior surface 76 of the inlet nozzle 70 defines a circumference sized sufficiently smaller than the diameter of the second flange 20 to compress the second flange from the position shown in FIG. 2 into a closed position shown in FIG. 1. In one exemplary embodiment, the internal ID of the inlet nozzle is about 0.5 mil to about 8 mils smaller than the normal closed diameter of the second flange 20 with a range of about 0.1 mil to about 3 mils being more preferred. This relative dimensions between the internal diameter of the inlet nozzle and the normal closed diameter of the second flange 20 create a seal at the inlet 72 for terminating fluid communication between the inlet 72 and the outlet (not shown) of the valve assembly 78. Although FIG. 6 shows the reduced section 32 located between the lower neck section 30 and the upper neck section 34 of the piston 10 being spaced apart from the shoulder 70 in the interior cavity of the inlet nozzle 70, in one exemplary embodiment the two contact one another to provide a second sealing point.

Figure 7:
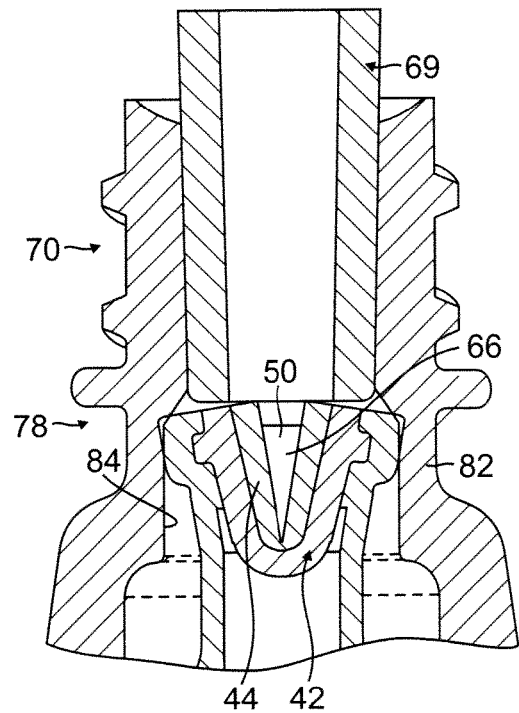
FIG. 7 is a semi-schematic partial cross-sectional side view of the valve of FIG. 6 with the piston urged distally into the valve housing and the actuator in an open position.

FIG. 7 is a semi-schematic partial cross-sectional side view of the valve assembly 78 of FIG. 6 in a second or open position with the tip 69 of the medical implement inserted into the inlet lumen of the inlet nozzle 70. The tip 69 exerts a downward pressure on both the inlet actuator 42 and the piston body 12 and pushes the two distally into the interior cavity of the valve housing 68. As discussed in the '838 patent, which was previously incorporated herein by reference, when the piston 10 moves to its second position, the piston body 12 collapses under the pressure of the tip 69 into random folds. In one exemplary embodiment, the collapsing piston body changes the space occupied by the piston a sufficient amount to create a negative bolus effect or negative flush, represented by small amount of fluid entering into the interior cavity of the valve as the piston moves to its second position.

Figure 8:
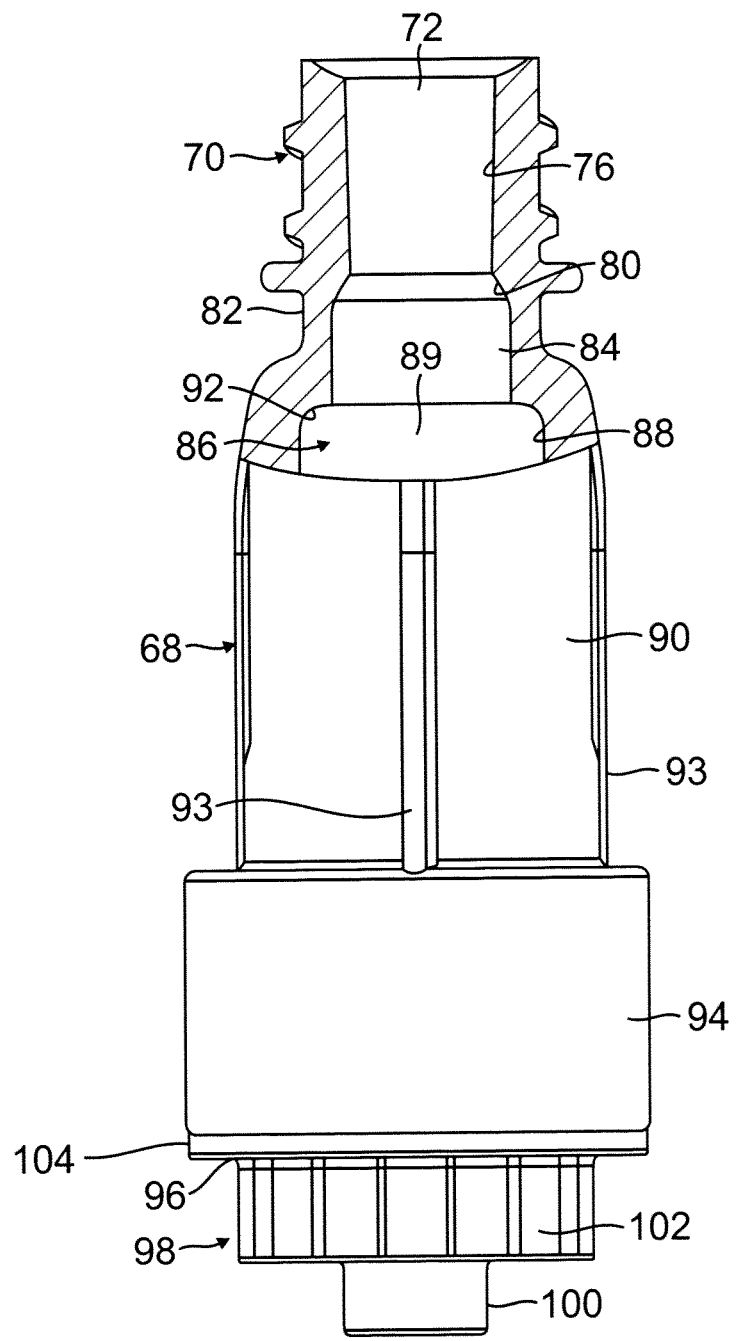
FIG. 8 is a semi-schematic partial side view and partial cross-sectional view of a valve housing provided in accordance with aspects of the present invention.

The inlet actuator 42 moves to an enlarged lower neck section 82 of the valve housing 69, which defines an interior circumference 84 that is larger than the interior circumference 76 of the upper inlet nozzle section 70. The larger lower neck section 82 provides sufficient space to enable the inlet actuator 42 to expand, which separates the seam 50 to create a flow path or gap 66 for fluid flow either from the medical implement or towards the medical implement. Assuming fluid is delivered by the medical implement, fluid flow will flow out the tip 69, through the gap 66 formed at the seam 50, and out through the two sides of the seam. Fluid then travels in the space between the interior wall surface of the valve housing 68 and the exterior surface of the piston 10 and out the valve outlet (not shown). Upon removal of the tip 69 from the inlet nozzle 70, the piston 10 expands due to the resilient characteristics of material used to form the piston 10, which returns to the position shown in FIG. 6. In one exemplary embodiment, a positive bolus effect is created when the piston 10 expands to its first position, characterized by a small amount of fluid being pushed out the outlet from the interior cavity of the valve, FIG. 8 is a semi-schematic partial cut-away side view of an exemplary valve housing 68 provided in accordance with aspects of the present invention, shown without a piston. With reference to FIG. 8 in addition to FIG. 7, the interior cavity 86 has yet another enlarged interior circumference 88 defined by the main body section 90 of the valve housing 68. The lower larger interior circumference 88 comprises a lower generally round or curved shoulder 92. In one exemplary embodiment, the curved shoulder 92 is provided for mating contact with the first shoulder 28 on the piston body 12, to provide another sealing point.

In one exemplary embodiment, the interior circumference 88 of the main body section 90 has a smooth surface. The interior circumference 88 defines a main interior diameter 89 having a generally constant diameter extending over a majority of the main body section, which in one exemplary is generally constant from just distal of the lower shoulder section 92 to about the interface of the main body section 90 and the skirt 94. In one exemplary embodiment, the main interior diameter 89 is sized sufficiently larger than the diameter of the body section 17 of the piston 10 (FIG. 1) so that fluid flow delivered through the inlet opening 72 of the valve housing 68, or from the outlet of the valve housing towards the inlet opening for taking samples through the valve, has sufficient fluid flow space to flow out the valve outlet 100.

Exteriorly, the valve housing 68 incorporates a plurality of ribs 93, which in one exemplary embodiment includes four equally spaced apart ribs. A downwardly extending skirt 94 depends from the main body section 90 and terminates in a lower opening 96 for receiving a nut fitting 98. As discussed in the '838 patent, the nut fitting 98 includes an outlet port 100 for outputting fluid delivered through the inlet opening 72 and a threaded collar 102 for threaded engagement with a second medical implement (not shown), which may be a tubing adaptor, a catheter, or the like. The nut fitting 98 may be ultrasonically welded or alternatively glued to the skirt 94 by either welding or gluing a flange 104 on the nut fitting 98 with the end edge of the skirt 94.

Figure 9:
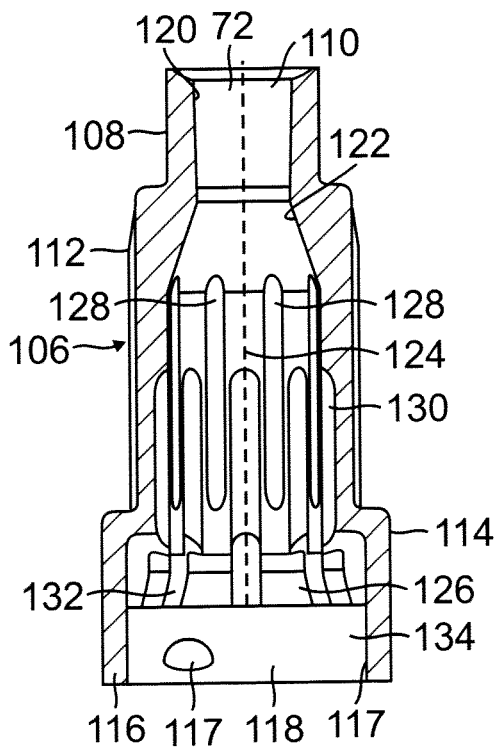
FIG. 9 is a semi-schematic partial side view of another valve housing provided in accordance with aspects of the present invention.

FIG. 9 is a semi-schematic cross-sectional side view of an alternative valve housing 106 provided in accordance with aspects of the present invention. In one exemplary embodiment, the valve housing 106 comprises an inlet nozzle 108 defining an inlet opening 72, a main body section 112, and a skirt 114 depending therefrom having an end edge 116 defining a lower housing opening 118.

Interiorly, the valve housing 106 comprises an upper inlet section or upper neck section 120, a tapered section or lower neck section 122, a main interior body section 124, and an interior skirt section 126. In one exemplary embodiment, the interior body section 124 comprises a plurality of raised ribs 128, which both protrude above the interior wall surface of the interior body section 124, and a plurality of indentations 130, which recess below the interior wall surface of the interior body section. The raised ribs 128 and the indentations 130 provide flow paths or channels for fluid flow flowing from inlet to the outlet of the valve, in between the space defined by the interior wall surface of the valve housing and the exterior surface of the piston.

In one exemplary embodiment, a plurality of lower indentations 132 are incorporated in the interior wall surface 134 of the skirt section 114. The lower indentations 132 are preferably aligned with the upper indentations 130 so that fluid flow through the upper indentations will flow to the lower indentations on its way towards the outlet. In one exemplary embodiment, eight raised ribs 128, eight upper indentations 130, and eight lower indentations 132 are incorporated. The ribs and the indentations are preferably equally spaced apart from one another. Also shown formed on the skirt section is a positioner 117 for positioning the nut fitting. In one exemplary embodiment, three spaced apart positioners are incorporated.

Figure 10:
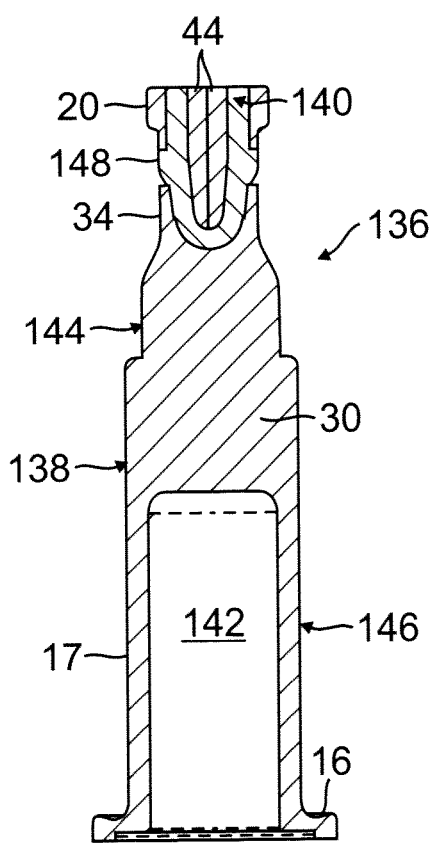
FIG. 10 is a semi-schematic cross-sectional side view of an alternative valve piston provided in accordance with aspects of the present invention, which has an inlet actuator configured to open and close the upper section of the piston to create a fluid flow path.

FIG. 10 is a semi-schematic cross-sectional side view of an alterative piston 136 provided in accordance with aspects of the present invention. The piston 136 is configured to work with a valve housing, such as that shown in FIGS. 6-9, to regulate fluid flow from between the inlet and the outlet of the valve housing, or for flow in the reverse direction. In one exemplary embodiment, the piston 136 comprises a piston body 138 defining an interior cavity 142 and an inlet actuator 140. The piston body 138 is similar to the piston body disclosed with reference to FIGS. 1, 2, and 5 with a few exceptions. In the present embodiment, the upper neck section 34, the lower neck section 30, and part of the body section 17 are solidly form from the same material as the piston wall, which are herein collectively referred to as the upper piston core 144. The body section 17 circumscribing the cavity 142 is herein referred to as the pliable and resilient piston base 146. The inlet actuator 140 in the present embodiment, like the inlet actuator 42 of the FIG. 1 embodiment, comprises a projection 148 configured to be exposed through the upper neck section 34.

When the piston 136 is installed inside a valve housing and compressed during operation, the pliable and resilient piston base 146 is configured to buckle and contort in random fashion to accommodate the tip of a medical implement. In one exemplary embodiment, the pliable and resilient piston base 146 is configured to recoil when the medical implement is removed unaided by a spring or other independent biasing member. By selecting an elastomer or a TPE with sufficient resiliency, wall thickness, and hardness, the pliable piston base 146 may exhibit sufficient springing characteristics that will allow it to recoil without a separate spring. However, as is readily apparent to a person of ordinary skill in the art, a coil spring may be placed inside the interior cavity 142 to facilitate piston recovery, as discussed in the '838 patent.

Figure 11:
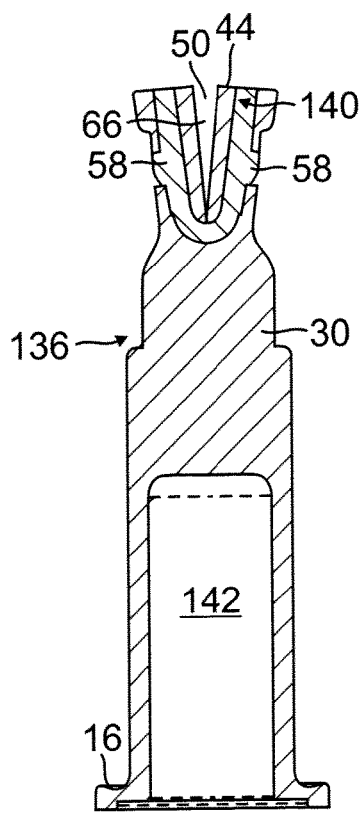
FIG. 11 is a semi-schematic cross-sectional side view of the valve piston of FIG. 10 with the inlet actuator in an open position.

FIG. 11 is a cross-sectional side view of the piston 136 of FIG. 10, shown with the inlet actuator 140 in its normal state outside of a valve housing. As clearly shown, the two extensions 58 are spaced apart from one another, which opens up a gap at the seam 50 for fluid flow, as previously discussed.

Figure 12:
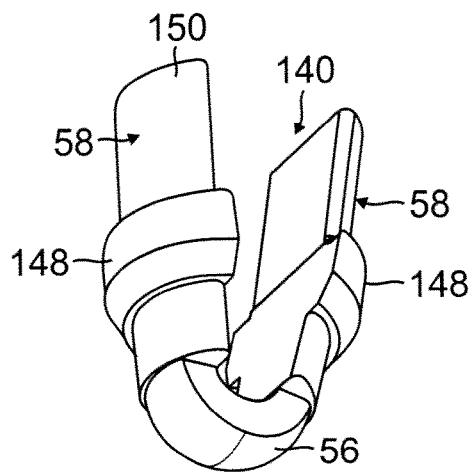
FIG. 12 is a semi-schematic perspective view of an alternative actuator provided in accordance with aspects of the present invention.

FIG. 12 is a semi-schematic perspective view of the inlet actuator of FIGS. 10 and 11. The two extensions 58 each comprises an extended leg 150. In one exemplary embodiment, the piston body 138 is molded over the inlet actuator 140 by first placing the inlet actuator in a mold cavity, placing a core pin therein, placing a thin sheet in between the two extensions and then injection molding the mold with an elastomer or a TPE. Following the injection process, the piston is removed and the seam 50 created in the overmolding process.

Figure 13:
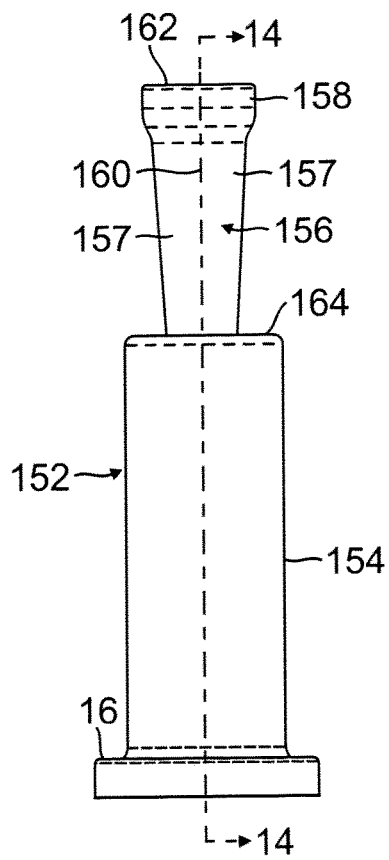
FIG. 13 is a semi-schematic side view of yet another valve piston provided in accordance with aspects of the present invention; which incorporates a slit at the neck section of the piston.

FIG. 13 is a semi-schematic side view of yet another embodiment of a piston 152 provided in accordance with aspects of the present invention. In one exemplary embodiment, the piston 152 comprises a lower flange 16, a body section 154, and a neck section 156 comprising an upper flange 158. A slit 160 is incorporated approximately along the center of the neck section 156 to define two piston neck extensions 157. The slit 160 extends between the upper top surface 162 of the piston and a shoulder 164 at the upper edge of the body section 154. The slit 160 defines a seam having a plane that can open or close to form a gap depending on the position of the piston 152 when inside a valve housing. Preferably, the slit 160 is aligned along the lengthwise axis of the piston. However, the slit 160 can extend transversely of the lengthwise axis of the piston without deviating form the spirit and scope of the present invention.

Figure 14:
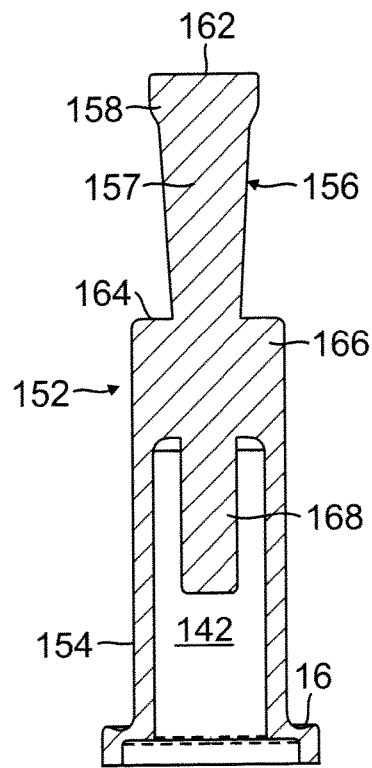
FIG. 14 is a semi-schematic cross-sectional side view of the piston of FIG. 13 taken along line 14-14.
Figure 39A:
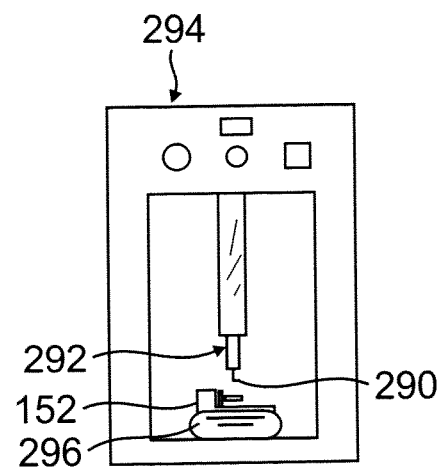
FIG. 39A is a semi-schematic general depiction of an ultrasonic generator equipped with a cutting blade.

FIG. 14 is a cross-sectional side view of the piston of FIG. 13 taken along line 14-14. In one exemplary embodiment, the neck section 156 is molded as a solid structure throughout with the slit 160 formed subsequent to the molding step by a cutting process. Exemplary cutting processes include cutting the neck section with a thin blade, by laser cutting, or by water jet cutting. With reference to FIG. 39, in one implementation of the present invention, a thin blade 290 in the order of about 0.015 inch to about 0.03 inch thick with a sharpened edge, preferably of an exotic metal such as titanium, is used to cut the slit 160. The blade is mounted to a coupler or shaft 292, which is connected to a prior art ultrasonic generator 294, preferably with an operating range of about 20 kHz to about 40 kHz. An exemplary generator includes the Branson 2000aed model. The piston 152 is then placed in a fixture 296, such as a base or drum, with the neck section directly adjacent the blade 290. The ultrasonic generator 294 is then energized while simultaneously moving the blade co-axially into the piston, if the piston was held vertical, or perpendicular to the piston centerline, if the piston was held horizontally. Once the slit 160 has been made, the blade is de-energized and withdrawn back away from the piston. Alternatively, the vibrating blade may be held fixed and the piston, mounted on the base or drum 296, moved into the vibrating blade to create the slit.

A solid upper body section 166 extends distal of the neck section 156 with a stop pin 168 extending distally thereof into the interior cavity 142 of the body section 154. The stop pin 168 is configured to restrict over-insertion of the medical implement by providing a physical stop and strict the amount inward collapse of the piston wall into the interior cavity 142 when buckled by the medical implement from the top and a nut fitting from below.

Figure 15:
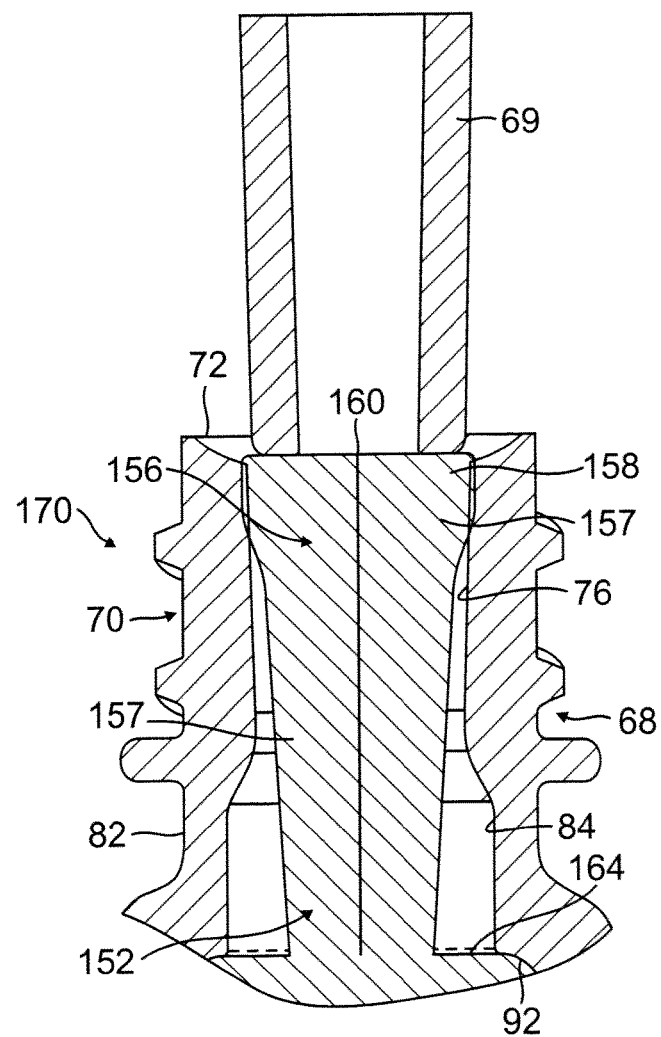
FIG. 15 is a semi-schematic partial cross-sectional side view of a valve assembly provided in accordance with aspects of the present invention; which comprises the piston of FIG. 13 positioned inside a valve housing.

FIG. 15 is a partial cross-sectional side view of the piston 152 mounted inside a valve housing 68 forming a valve assembly 170. The piston 152 is shown in a first or closed position with the upper flange 158 compressed against the interior wall surface of the inlet nozzle 70, which functions to seal the valve 170 and closes fluid communication between the inlet opening 72 and the outlet (not shown). The piston shoulder 164 also abuts the lower shoulder 92 of the valve housing 68 to provide another sealing point.

Figure 16:
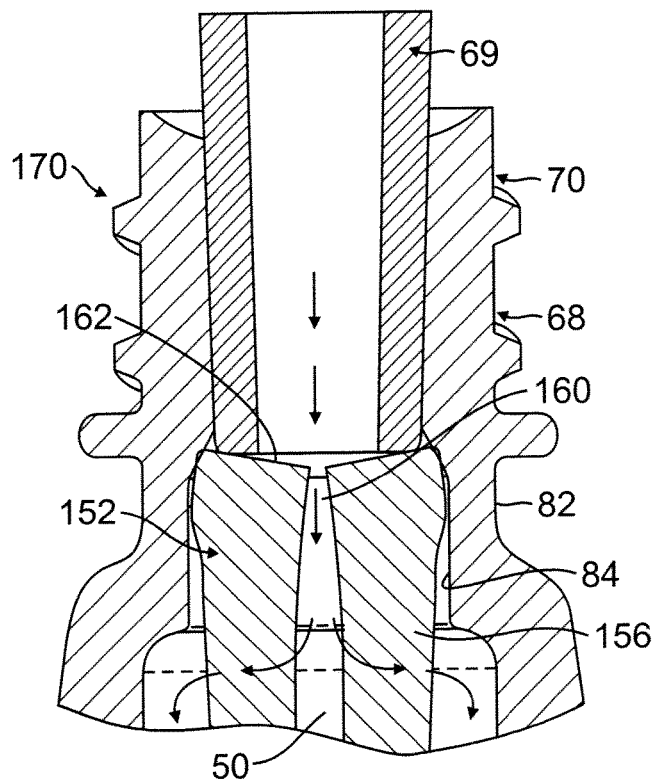
FIG. 16 is a semi-schematic partial cross-sectional side view of the valve assembly of FIG. 15 with the piston moved to a second position by a tip of a medical implement.

FIG. 16 is a semi-schematic partial cross-sectional side view of the valve assembly 170 of FIG. 15 pushed by a tip 69 of a medical implement to a second or used position. The tip 69 pushes the upper top surface 162 of the piston 152 into the interior section 84 of the enlarged lower section 82 of the inlet nozzle 70. Due to the larger interior space at the enlarged lower section 82, the two piston neck extensions 157 are forced apart, which may be described as a buckling effect caused by the medical implement and the stop pin 168, so that a gap 66 is formed at the seam 50. At this point, fluid delivered by the medical implement will flow out of the tip 69, through the seam 50, and then around the outside surface of the piston 152 and the interior surface of the valve housing 68. Conversely, if a sample is to be taken, flow will flow in between the space defined by the interior surface of the valve housing and the exterior surface of the piston, then through the seam 50 and in through the tip 69.

The piston 152 automatically moves from the second position (FIG. 16) to the first position (FIG. 15) upon removing the tip 69 from the inlet nozzle 70. The piston body section 154 automatically recovers due to its inherent resilient characteristic. Alternatively, as previously discussed, a coil spring may be used to facilitate recovery.

Figure 17:
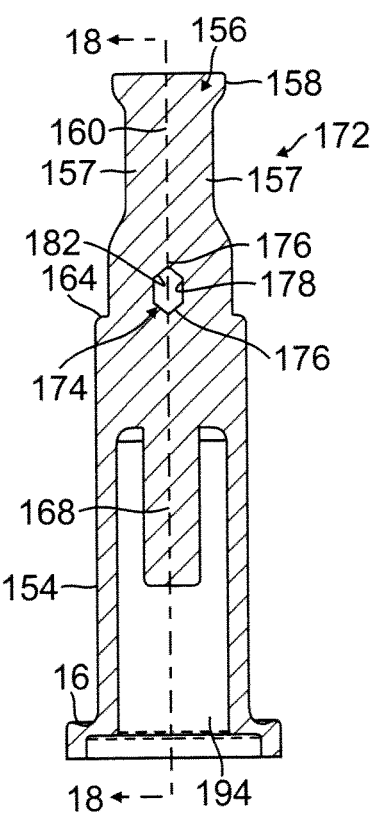
FIG. 17 is a semi-schematic side view of yet another valve piston provided in accordance with aspects of the present invention; which incorporates a slit at the neck section of the piston having a through-hole.

FIG. 17 is a semi-schematic cross-sectional side view of yet another piston 172 provided in accordance with aspects of the present invention. In one exemplary embodiment, the alternative piston 172 is similar to the piston 152 disclosed in FIGS. 13 and 14 with a few exceptions. For example, the piston 172 incorporates a slit 160, which defines a seam and separates the neck section 156 into two piston neck extensions 157, and a stop pin 168. In the present embodiment, a through-hole 174 having a polygonal cross-section is formed along at least a portion of the through-hole. In a preferred embodiment, the through-hole 174 is a six-sided polygon orientated so that two vertices 176 are aligned lengthwise in the same direction as the vertical slit 160. The through-hole 174 is formed so that half of the through-hole is formed on one piston neck extension 157 and the other half is on the other piston neck extension.

Figure 18:
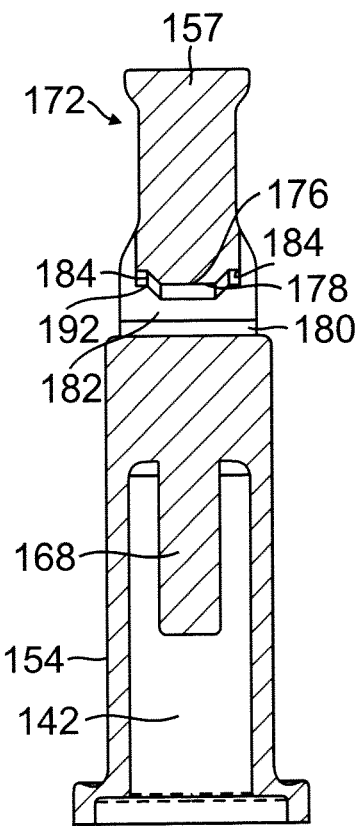
FIG. 18 is a semi-schematic cross-sectional side view of the piston of FIG. 17 taken along line 18-18.

Referring now to FIG. 18, which is a cross-sectional side view of the piston 172 of FIG. 17 taken along line 18-18. In one exemplary embodiment, the through-hole 174 is formed by molding a tapered upper surface 178 and a molded tapered lower surface 180 spaced apart from one another by a side surface 182. The tapered upper surface 178 is configured to abut a cross-rib located inside a valve housing, which acts to impart a pair of component forces on the tapered surface to push the piston neck extension 157 outwardly, as further discussed below. The lower tapered surface area 180 has a similar contour as a lower surface of the cross-rib, as further discussed below, and is configured to hug the lower surface when in a piston first position.

Figure 21:
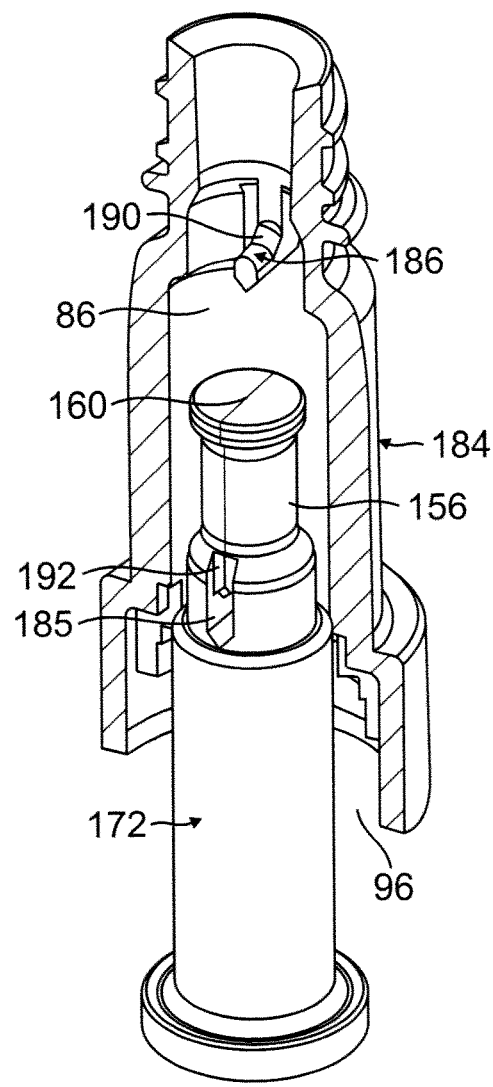
FIG. 21 is a semi-schematic partial perspective expanded view of the piston of FIG. 17 positioned inside the cavity of the valve housing of FIG. 19.

In one exemplary embodiment, the upper tapered surface 178 has a length that is relatively shorter than the length of the lower tapered surface 180. This relative dimension creates an exposed through-hole area 185 at each end thereof. The two exposed ends 185, as shown with reference to FIG. 21, are configured to receive a respective end of the cross-bar located inside the valve housing. However, as readily apparent to a person of ordinary skill in the art, the two exposed ends 185 (FIG. 21) may differ in shape, size, and contour depending on the shape, size, and contour incorporated for the cross-bar, which can vary depending on a designer's choice.

Figure 19:
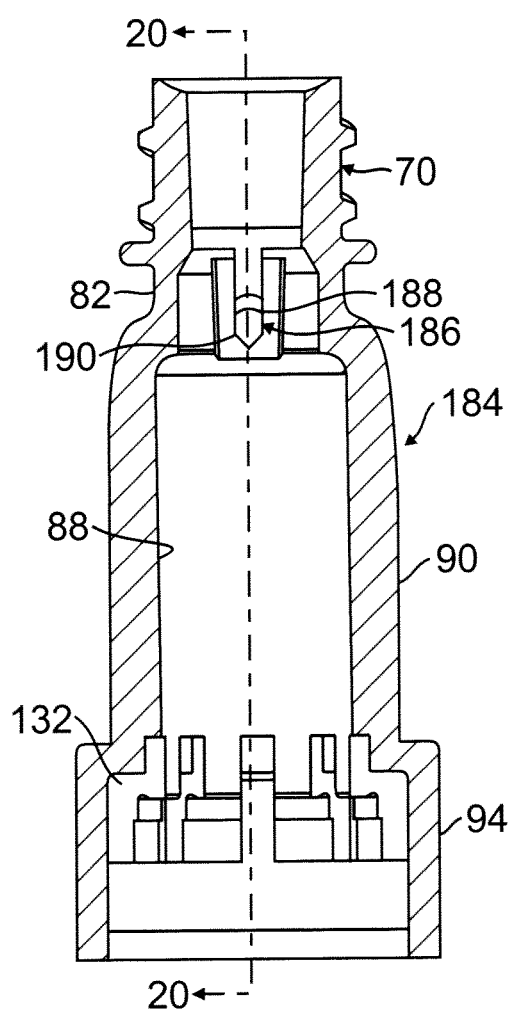
FIG. 19 is a semi-schematic cross-sectional side view of an alternative valve housing provided in accordance with aspects of the present invention, which incorporates a cross-bar at a lower neck section of the inlet nozzle.

FIG. 19 is a semi-schematic cross-sectional side view of a valve housing 184 provided in accordance with aspects of the present invention. The valve housing 184 is similar to the valve housing discussed with reference to the valve housing of FIGS. 8 and 9 with a few exceptions. Among the differences, a cross-bar 186 is incorporated in the interior cavity of the enlarged lower section 82 of the inlet nozzle 70. In one exemplary embodiment, the cross-bar 186 comprises a generally round upper mid-section 188 and a V-shaped bottom section 190 comprising an apex. The cross-bar is preferably integrally molded with the valve housing 184.

In one exemplary embodiment, the internal circumference 88 of the main body section 90 comprises a flat or smooth interior wall surface. However, raised ribs or flow indentations or both may be incorporated without deviating from the spirit and scope of the present invention. In one exemplary embodiment, a plurality of lower indentations 132 are formed on the skirt section 94 of the valve housing.

Figure 20:
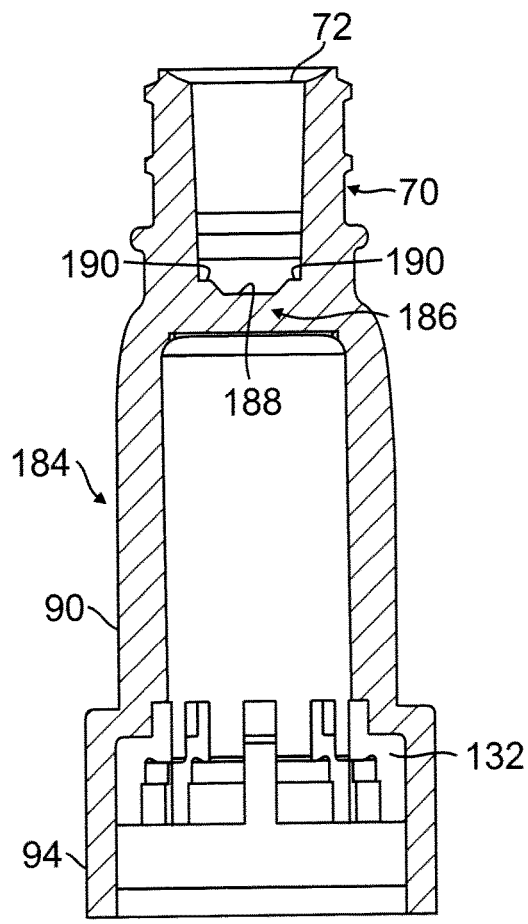
FIG. 20 is a semi-schematic cross-sectional side view of the valve housing of FIG. 19 taken along line 20-20.

FIG. 20 is a cross-sectional side view of the valve housing 184 of FIG. 20 taken along line 20-20. The cross-bar 186 has a round upper mid-section 188, as previously discussed, and two inclined ends 190 that correspond with inclined ends 192 located on the through-hole 174 of the piston 172. As is readily apparent to a person of ordinary skill in the art, the inclined ends 190, 192 on the valve housing and the piston, respectively, may be modified or eliminated without deviating from the spirit and scope of the present invention, such as making the round mid-section 188 extending the whole length of the cross-bar. Still alternatively, a cross-bar having a single distinct upper apex, different curvatures, or multiple vertices may be incorporated.

FIG. 21 is a semi-schematic partial perspective cut-away view of the piston 172 of FIG. 18 placed partially inside the valve housing 184 of FIG. 20. The piston 172 is configured to be inserted into the interior cavity 86 of the valve housing 184 by inserting the neck section 156 in through the end opening 96 of the valve housing 184 and aligning the slit 160 with the cross-bar 186. The piston is then pushed proximally until the cross-bar is seated inside the through-hole 174. Once seated, the two inclined ends 190 of the cross-bar is cradled inside the two exposed through-hole areas 185. In one exemplary embodiment, a rod (not shown) is used to push the piston 172 inside the housing. The rod may be inserted through the open end 194 (FIG. 17) of the piston and pushed against the stop pin 168.

Figure 22:
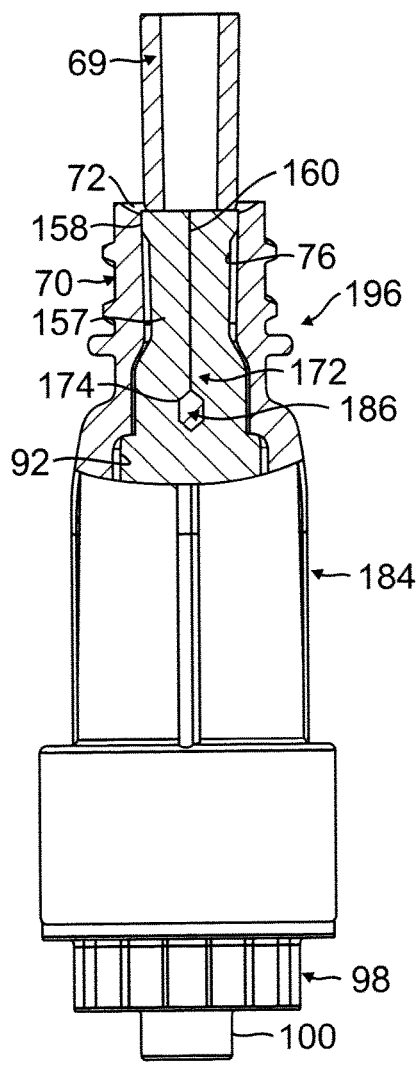
FIG. 22 is a semi-schematic partial cross-sectional partial side view of an alternative valve assembly provided in accordance with aspects of the present invention; which includes the piston of FIG. 17 positioned inside the valve housing of FIG. 19 and with a tip of a medical implement placed in contact with a top surface of the piston.

FIG. 22 is a partial cut-away side view of a valve assembly 196 comprising a piston 172, a valve housing 184, and a nut fitting 98. The piston 172 is shown in a first or closed position wherein the upper flange 158 is compressed against the interior surface 76 of the inlet nozzle 70 to both squeeze the two piston neck sections 157 together and terminate fluid flow from between the inlet opening 72 and the outlet port 100. A second seal is provide by the shoulder 164 of the piston 172 abutting against the lower shoulder 92 in the interior cavity 86 of the valve housing.

Figure 22A:
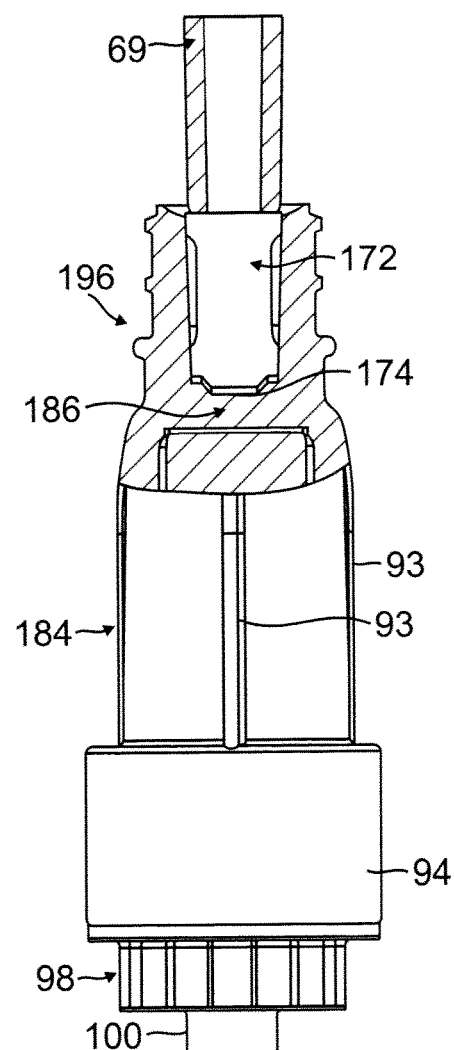
FIG. 22A is a semi-schematic partial cross-sectional partial side view of the valve assembly of FIG. 22 taken from a view rotated ninety degrees along the longitudinal axis of the valve housing.

FIG. 22A is a partial cut-away side view of the valve assembly 196 of FIG. 22 viewed from an orthogonal viewing plane.

Figure 22B:
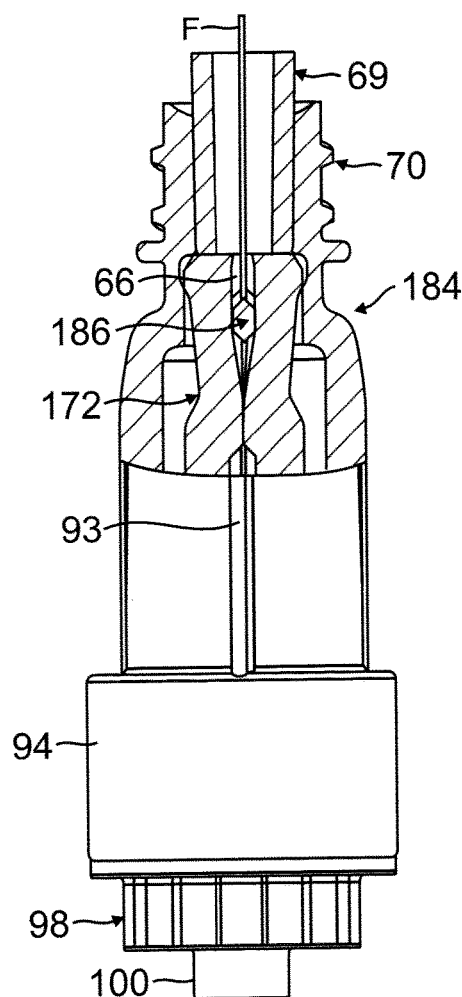
FIG. 22B is a semi-schematic partial cross-sectional partial side view of the valve assembly of FIG. 22 with the piston moved to a second used position by the tip of the medical implement to open a flow path for fluid flow from between the inlet and the outlet of the valve assembly.

FIG. 22B is a partial cut-away side view of the valve assembly 196 of FIGS. 22 and 22A in a second or used position. The tip 69 of the medical implement projects into the bore of the inlet nozzle 70 to compress the piston 172. As previously discussed, the force imparted by the tip causes the body section 154 (FIG. 17) of the piston to buckle and contort in random folds. Concurrently therewith, the slit 160 is forced over the cross-bar 186, which then separates the slit 160 to enlarge a gap 66. Flow F delivered by the medical implement flows through the tip 69 and passes through the gap 66 formed at the seam 50 before flowing out through the two sides of the seam and over the exterior surface of the piston 172 towards the outlet 100. Following the delivery of fluid through the medical implement, the tip 69 is removed from the inlet nozzle 70, which concurrently removes the force acting on the top surface of the piston. This allows the piston 172 to recover to its less compressed state, shown in FIGS. 22 and 22A.

As previously discussed, the piston 172 may be self-resilient and moves from a second position to a first position un-aided by a spring or an independent biasing member. However, a spring or an independent biasing member may be placed inside the interior cavity 142 of the piston 172 to facilitate recover of the piston from the second position towards the first position.

Figure 23:
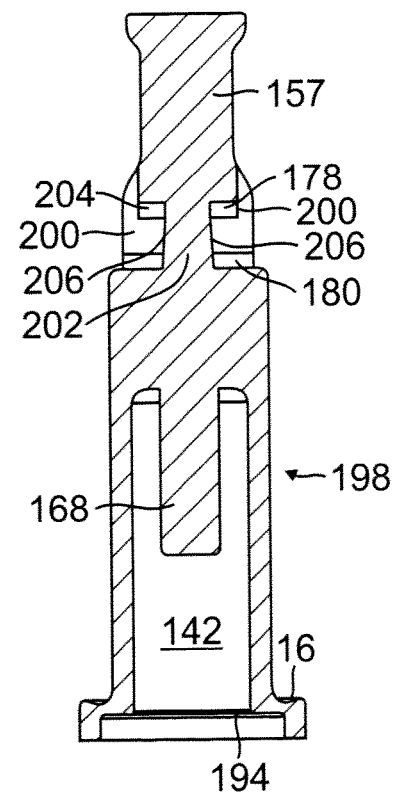
FIG. 23 is a semi-schematic cross-sectional side view of yet another alternative valve piston provided in accordance with aspects of the present invention.

FIG. 23 is a semi-schematic cross-sectional side view of yet another piston 198 provided in accordance with aspects of the present invention. The present piston 198 embodiment shares a lot of similarities with the piston 172 shown in FIGS. 17, 18, 20, and 22. However, whereas the piston 172 shown in FIGS. 17, 18, 20, and 22 incorporate a through-hole 174, the present piston 198 embodiment incorporates a dividing wall 202 at the through-hole to define two cavities 200. The two upper ends 204 of the two cavities 200 have also been modified to terminate in simple rounded corners. In one exemplary embodiment, the dividing wall 202 comprises two tapered wall surfaces 206 that extend outwardly as the wall span from a proximal position to a distal position.

Each cavity 200 comprises a tapered upper surface 178 and a tapered lower surface 180, similar to the through-hole 174 disclosed with reference to FIG. 18.

Figure 24:
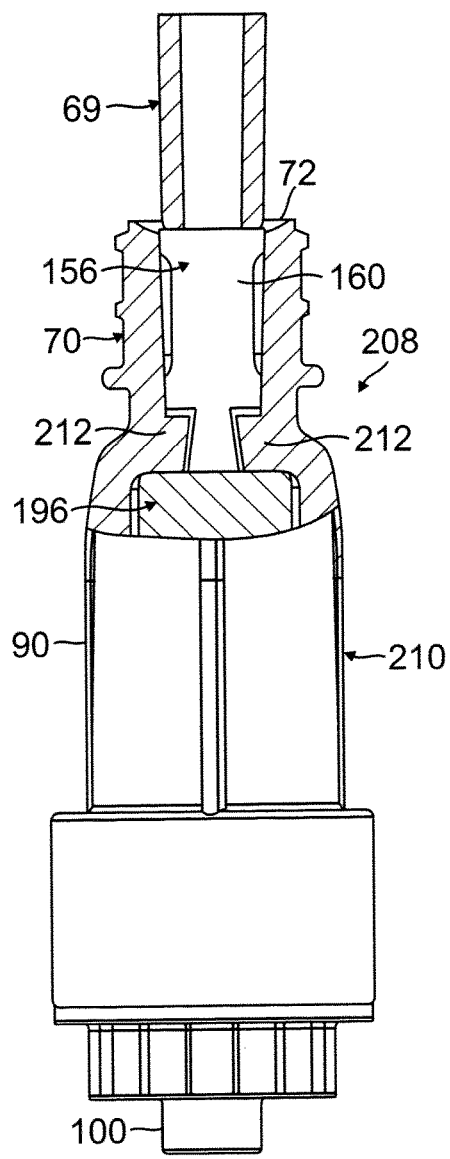
FIG. 24 is a semi-schematic partial cross-sectional partial side view of yet another alternative valve assembly provided in accordance with aspects of the present invention; which includes the piston of FIG. 23 positioned inside a valve housing having corresponding extensions for cooperating with a pair of cavities located on the piston.

FIG. 24 is a partial cut-away side view of a valve assembly 208 provided in accordance with aspects of the present invention, which comprises the piston 198 shown in FIG. 23 mounted inside a valve housing 210. In one exemplary embodiment, the valve housing 210 is similar to the valve housing discussed above with reference to FIGS. 19 and 20 with a few exceptions. In the present embodiment, the interior cavity of the housing, at the junction between the inlet nozzle 70 and the main body section 90, comprises two rib extensions 212 rather than a continuous cross-bar 186. The two rib extensions 212 are sized to project into the two cavities 200 (FIG. 23) and the two cavities are sized to accommodate the two rib extensions.

In use, a tip 69 of a medical implement is inserted into the lumen defined by the inlet nozzle 70, which then exerts a force on the piston 198. The downward force on the piston 198 pushes the two cavities 200 against the two rib extensions 212, which then act on the tapered upper surface 178 of the two cavities to split the neck section 156 along the slit 160 to open up a gap at the slit. The gap provides fluid flow path for fluid flow between the inlet opening 72 and the outlet 110.

Following an injection and after the tip 69 is removed from the inlet nozzle, the piston 70 recovers to its less compressed state by moving from the second position to the first position. As before, a spring or an independent resilient member may optionally be used with the piston 198 to facilitate recovery after the tip 69 is removed.

Figure 25:
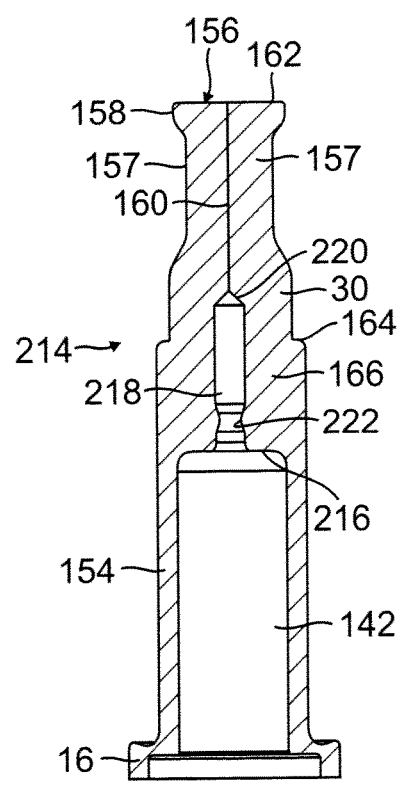
FIG. 25 is a semi-schematic cross-sectional side view of still yet another alternative valve piston provided in accordance with aspects of the present invention.

FIG. 25 is a semi-schematic cross-sectional side view of yet another alternative piston 214 provided in accordance with aspects of the present invention. In one exemplary embodiment, the piston 214 comprises a slit 160 that separates the neck section 156 into two piston neck extensions 157, as with other previously discussed pistons. The piston 214 also comprises a body section 154 and a lower flange 16. The body section 154 defines an interior cavity 142 that comprises a top wall surface 216 and a spike bore 218. The spike bore 218 extends proximally from the top wall surface through the upper body section 166 and part of the lower neck section 30.

In a preferred embodiment, the spike bore 218 terminates in an apex 220 with the tip of the apex in communication with the slit 160, when the latter opens. In one exemplary embodiment, the bore 218 comprises a single diameter cylindrical bore. Preferably however, one or more reduced neck sections 222 are incorporated in the bore 218 to act as sealing rings around an activating pin, as further discussed below.

Figure 26:
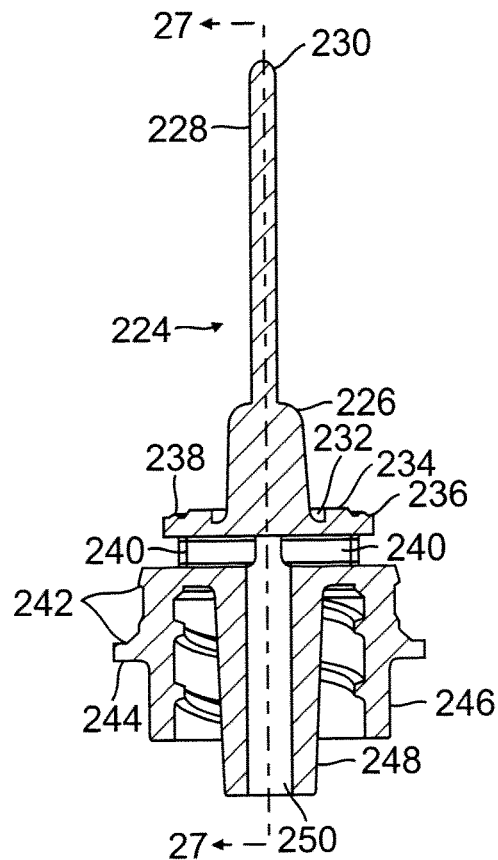
FIG. 26 is a semi-schematic cross-sectional side view of a nut assembly for mating with a valve housing provided in accordance with aspects of the present invention.

FIG. 26 is a semi-schematic cross-sectional side view of a nut fitting 224 provided in accordance with aspects of the present invention. In one exemplary embodiment, the nut fitting 224 is similar to the nut fitting disclosed in the '838 patent with the exception of the central projection 226, which has an elongated activating pin 228 having a rounded tip 230. Other features of the nut fitting 224 include a circular channel 232, a raised floor 234, and a seal seat 236 comprising an optional projection 238, analogous to a raised face flange. Further distally, the nut fitting 224 includes two spaced apart liquid passages 240, a skirt section 246 that comprises one or more position members 242, a flange 244, and a discharge nozzle 248 comprising a lumen 250.

Figure 27:
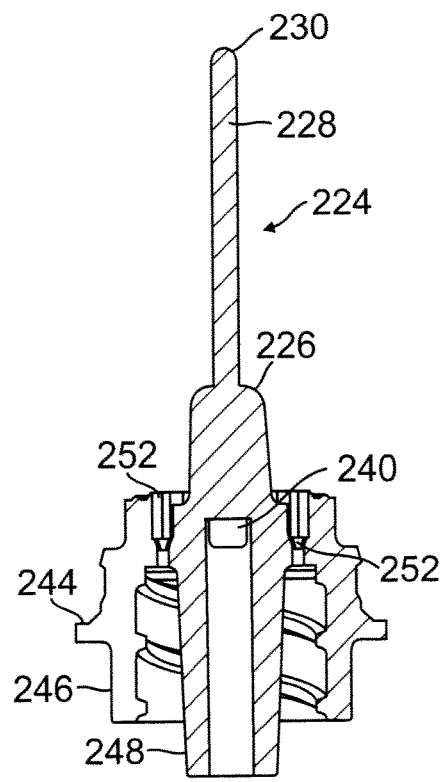
FIG. 27 is a cross-sectional side view of the nut assembly of FIG. 26 taken along line 27-27.

FIG. 27 is a cross-sectional side view of the nut fitting 224 of FIG. 26 taken from line 27-27. A pair of vent ports 252 are incorporated for venting air trapped inside the interior cavity 142 of the piston 214 when the latter is compressed by a tip of a medical implement, as discussed in the '838 patent. In one exemplary embodiment, the two vent ports 252 are spaced 180 degrees apart from one another and are each located in between two liquid passages 240, which are also spaced 180 degrees apart from one another.

Figure 28:
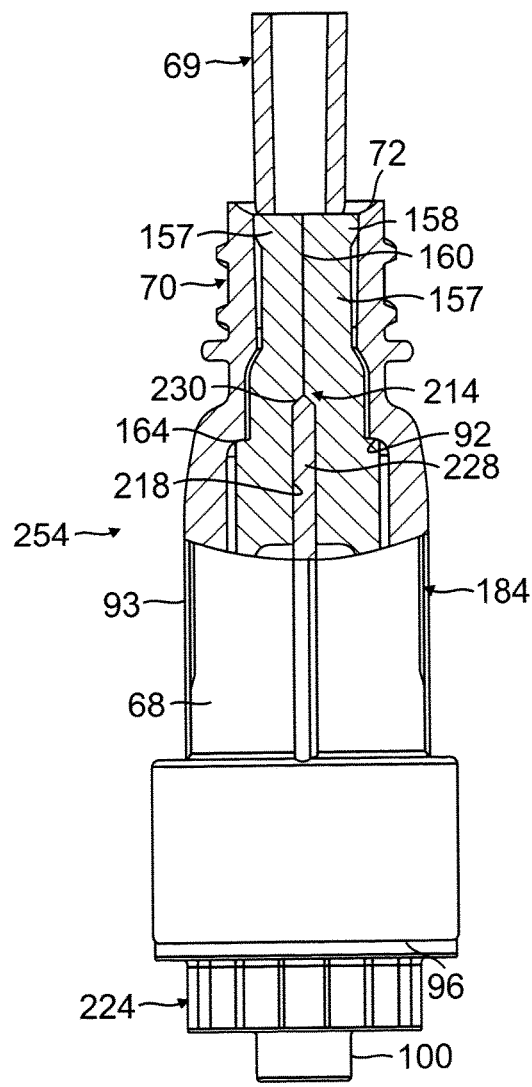
FIG. 28 is a semi-schematic partial cross-sectional partial side view of still yet another alternative valve assembly provided in accordance with aspects of the present invention; which includes the piston of FIG. 25 positioned inside a valve housing having the nut fitting of FIG. 26 coupled at the lower end of the valve housing.

FIG. 28 is a semi-schematic partial cut-away side view of a valve assembly 254 provided in accordance with aspects of the present invention, which comprises the piston 214 shown in FIG. 25 disposed in a valve housing 184 with the nut fitting 224 of FIGS. 26 and 27 secured to the lower opening 96 of the valve housing 68. In the piston first position shown, the upper flange 158 is sealed against the interior surface of the inlet nozzle and the piston shoulder 164 sealed against the lower shoulder 92 on the housing to terminate fluid communication between the inlet 72 and the outlet 100. The two piston neck extensions 157 are squeezed together to close the gap that would otherwise form at the slit 160.

The elongated activating pin 228 is disposed in the spike bore 218 of the piston with the rounded tip 230 positioned adjacent the distal most point of the slit 160. The bore 218 is preferably sized to have a neutral, i.e., no net interference, or somewhat loose fit, of about 0.5 to about 3 mil total clearance, around the pin 228.

Figure 29:
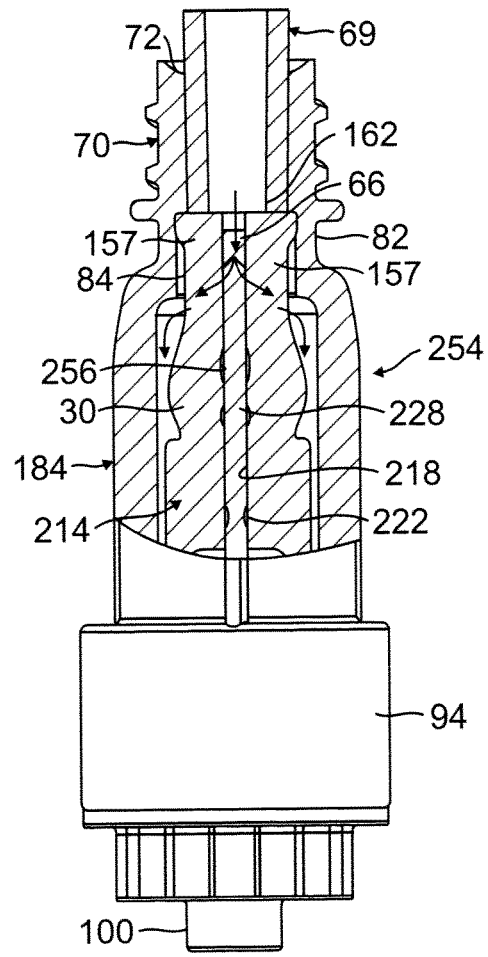
FIG. 29 is a semi-schematic partial cross-sectional partial side view of the valve assembly of FIG. 28 with the piston moved to a second position by a tip of a medical implement.

FIG. 29 is a semi-schematic partial cut-away side view of the valve assembly 254 of FIG. 28 in a second or used position, wherein the piston is in a more compressed state. The piston is moved to a used position by inserting a tip 69 of a medical implement into the inlet nozzle 70 of the valve housing 184 and causing the piston to collapse at the body section 154 (FIG. 25), which concurrently forces the bore 218 to move distally down the elongated activating pin 228 and the pin to move through the slit 160 to open a gap. Preferably the upper top surface 162 of the piston is moved sufficiently distally to the enlarged lower section 82 of the valve housing 184 where sufficient circumferential space is provided for the two piston neck sections 157 to separate. Fluid delivered through the valve 254 from a medical implement at this point will flow down the tip 69, through the gap 66, and out to the sides of the gap into the space between the exterior surface of the piston and the interior wall surface of the valve housing 184, as previously discussed.

To facilitate recovery of the piston 214 from the second position shown to a first position when the medical implement is removed from the inlet opening 72, either the piston 214 is sufficiently resilient to recover on its own and/or a resilient member is used to bias the piston to its first position, as previously discussed. In the present embodiment, friction between the activating pin 228 and the wall surfaces of the two piston neck extensions 157 at the slit 160 should be kept to a minimum. In one exemplary embodiment, residual fluid delivered to the valve acts as a lubricant to minimize friction. However, because the two piston neck extensions 157 deflect, a plurality of voids or uneven wall surfaces 256 are created adjacent the activating pin 228 to reduce friction between the activating pin and the wall surfaces of the two piston neck extensions 157.

Figure 30:
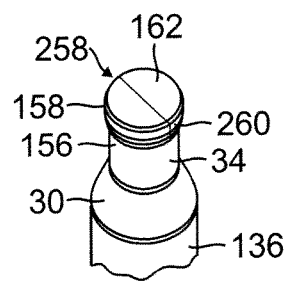
FIG. 30 is a partial semi-schematic perspective view of a piston in accordance with aspects of the present invention.
Figure 31:
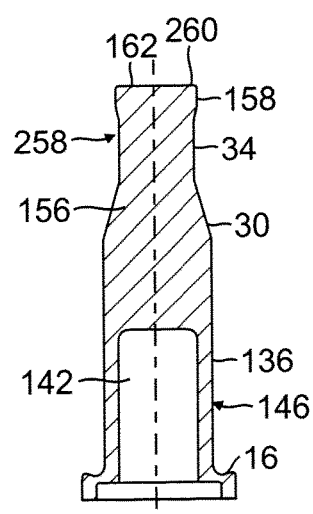
FIG. 31 is a cross-sectional side view of the piston of FIG. 33 taken along line 31-31.

FIG. 30 is a partial semi-schematic perspective view of a piston 258 in accordance with aspects of the present invention. FIG. 31 is a cross-sectional side view of the piston of FIG. 33 taken along line 31-31. In one exemplary embodiment, the piston 258 comprises an upper flange 158, a neck section 156 comprising an upper neck 34, a lower neck 30 and a piston body 136. The piston body 136 defines an interior cavity 142 with a pliable and resilient piston base 146, and a base flange 16. The piston 258 is configured to be used with a valve housing 302, such as, for example, the valve housing shown in FIG. 37, to operate as a needleless injection port valve.

Figure 30A:
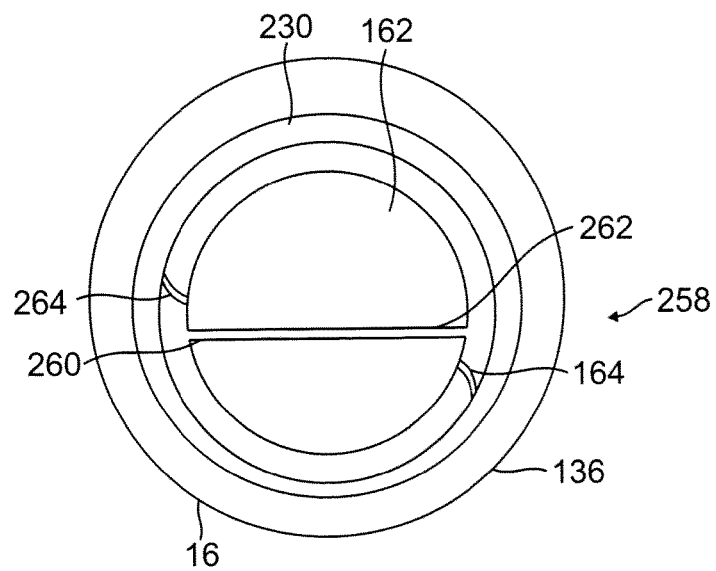
FIG. 30A is a partial perspective top view of the piston.
Figure 33:
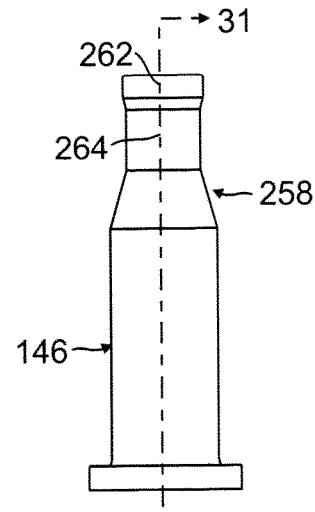
FIG. 33 is a semi-schematic side view of the piston of FIG. 32 taken from a view rotated 180 degrees along the longitudinal axis of the piston.

With reference now to FIG. 33 with continued reference to FIGS. 30 and 31, the piston 258 in accordance with aspects of the present invention incorporates a slit 260 created in a helical twist configuration for providing a fluid path through the neck section 156 when used in combination with the valve housing 302. In one embodiment, the slit 260 is formed above or proximal of the lower neck 30. In one exemplary embodiment, the slit 260 comprises an upper slit section 262 and two lower slit sections 264. Each of the lower slit sections 264 extend in opposite directions relative to the upper slit section 262 as if to wrap in a twisting manner at least partially around the circumference of the neck section 156 in opposite directions. The cut edges extend to the exterior surfaces of the neck section as shown in FIG. 30A. As further discussed below, when the piston is compressed, the slit 260 is forced to open, so that a gap is provided for fluid flow through the upper neck 34 of the piston. Thus, a piston provided herein is understood to include a solid upper piston section having a helical cut comprising two opposed leading cut edges that extend away from one another. Another aspect of the present invention is a piston comprising a slit formed across the entire upper neck section 34 such that the upper flange 158 is cut continuously from one outer edge to another out edge, as shown in FIG. 30. Note that while a gap is shown at the slit 260, due to the elasticity of the piston and the wall thickness of the cutting blade, the two sections can touch and only a single line can be seen.

Figure 32:
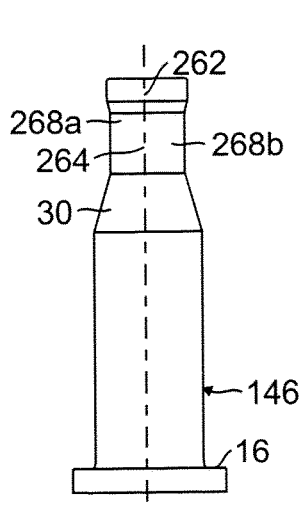
FIG. 32 is a semi-schematic side view of the piston of FIG. 31, which shows a helical slit configuration for providing a fluid flow path.

Referring now to FIG. 32 with continued reference to FIG. 33, in one embodiment, the upper slit section 262 and the lower slit sections 264 are formed post mold injection by a cutting process through a depth of about 0.100 to 0.180 inch measured from the top of the piston. However, other depths are possible when factoring in the durometer of the piston and the material. The cutting process may be better understood with reference to FIG. 39A. In one implementation of the present invention, a thin blade 290 with a sharpened edge made from metal such as titanium or stainless steel, is used to cut the slit 260. The blade is mounted to a coupler or shaft 292, which is connected to a prior art ultrasonic generator 294, preferably with an operating range of about 20 kHz to about 40 kHz. An exemplary generator includes the Branson 2000aed model. The piston 258 is then placed in a fixture 296, such as a base or drum, with the neck section directly adjacent the blade 290. The ultrasonic generator 294 is then energized while simultaneously moving the blade co-axially into the piston and rotating the blade. Once the slit 260 has been made, the blade is de-energized and withdrawn back away from the piston. Alternatively, the vibrating blade may be held fixed and the piston, mounted on the base or drum 296, moved into the vibrating blade to create the slit.

In one embodiment, the helical cut resembles a screw operation, which is the combination of a rotation by some angle about a longitudinal axis of the piston (called the screw angle), combined with a translation by some distance along the longitudinal axis of the piston. In this embodiment, the upper slit section 262 is created and aligned vertically along the longitudinal axis of the piston as the blade begins to translate through the neck section 156. The lower slit sections 264 are created as the advancing blade is made to rotate at an angle about the longitudinal axis of the piston. The lower slit sections 264 wrap partially around the circumference of the neck 156. The slit 260 divides the neck 156 into an upstream section 268a defined on one side or above the slit 260, and a downstream section 268b defined on the opposing side or below slit 260.

Figure 39B:
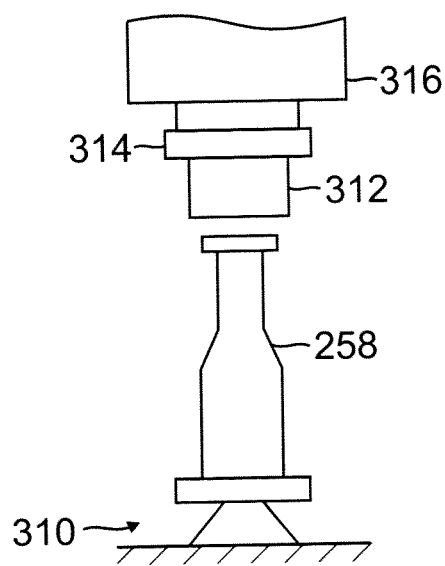
FIG. 39B is a simplified general depiction of a robotic cutter equipped with a cutting blade for cutting a seam or slit in a piston.

As shown in FIG. 39B, the cutting process for producing the helical slit 260 may also be performed by mounting the piston 258 in a fixture 310, such as a mounting pin or similar apparatus, in a vertical orientation with the open end of the piston 258 facing down. In this implementation, the cut is made using a straight single blade 312, made from, for example, stainless steel or similar material. The straight cutting blade 312 may have a wall thickness of about 0.010 to 0.015 inch, preferably about 0.014 inch. With the cutting side of the blade facing down, the blade may be mounted in a chuck 214 of a robotic cutter 316, such as, for example, a 3-axis Yamaha YK250X High Speed Scara Robot or any suitable equivalent. The robotic cutter 316 initially moves the blade 312 into a cutting position directly over the top and centerline of the vertically positioned piston 258. The blade is moved downward making a cut along the Z-axis of the piston 258. As it moves downward, the blade is rotated at a constant rate at an angle of rotation between about 20 to 90 degrees, creating a partial helix. It should be understood that the rotation of the blade may be either clockwise or counter-clockwise and the total depth measured from the top surface is about 0.100 to about 0.180 inch, which may vary depending on the material and durometer of the piston. In one embodiment, the cut is counter-clockwise so that when a syringe is inserted and rotated clockwise to engage the threads on the valve housing, the clockwise rotation facilitates opening the slit for fluid flow. Thereafter, the counter-clockwise rotation of the syringe to remove the syringe from the valve housing facilitates closing the slit.

Figure 34:
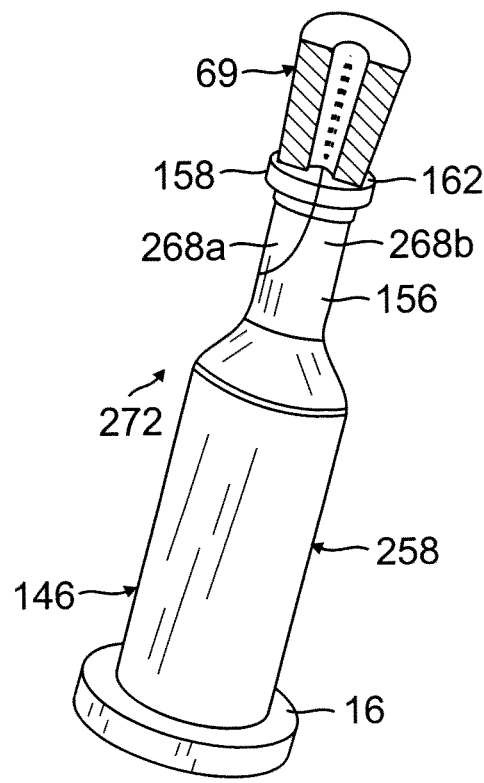
FIG. 34 is a semi-schematic partial cross-sectional partial perspective view of the piston of FIG. 31 positioned inside an invisible valve housing; which may include any one of the valve housings shown in FIGS. 6 and 9 and 37.

FIG. 34 is a semi-schematic perspective view of the piston 258 of FIGS. 30-33. FIG. 34 is a depiction of the piston 258 inside a valve housing, such as valve housing 302 (FIG. 37) forming a valve assembly 272 (the valve housing not shown in FIGS. 34-36 for clarity). In practice, however, the valve housing may be any one of the valve housings discussed hereinabove or as shown and discussed with reference to FIG. 37 hereinbelow. A partial cross-sectional perspective view of a tip 69 of a medical implement is shown positioned at the top surface 162 of the piston. Just prior to opening the valve assembly 272, the piston 258 is in a first or ready position, which blocks fluid flow from between the inlet and the outlet of the valve housing, as previously discussed. The upper flange 158 is circumferentially compressed against the interior wall surface of the inlet nozzle to hold piston neck sections 268a and 268b together, which compresses the slit 260 to close the fluid flow path, forming a fluid tight seal.

Figure 35:
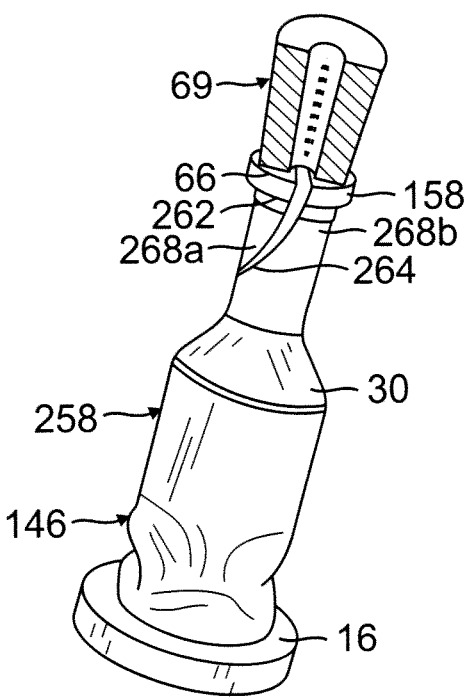
FIG. 35 is a semi-schematic partial cross-sectional partial perspective view of the piston of FIG. 34 moved towards a second position by a tip of a medical implement.

FIG. 35 is a semi-schematic perspective view of the valve assembly of FIG. 34 with the tip 69 partially inserted into the inlet nozzle of the valve housing. FIG. 35 is a depiction of the tip 69 being inserted into the inlet nozzle to a point into the valve housing where the slit 260 and the piston neck sections 268a and 268b of the piston are being compressed vertically along the longitudinal axis of the piston. The slit 260 provides relief for the neck 156 from the compression, such that the neck sections 268a and 268b begin to move or diverge relative to each other along the slit. As the piston is further compressed (FIG. 35), the gap formed by the two neck sections 268a, 268b further opens to form a conduit between the inlet and the outlet with part of the conduit provided by the interior surface of the housing. Thus, an aspect of the present embodiment is understood to include a valve comprising a piston having an upper neck section comprising a flange, a lower neck section, a body section, and a base flange located within a housing and wherein the piston is compressible and forms a flow path across an entire circumference of the flange of the upper neck section. The piston further forms a spiral flow path through at least a portion of the neck section such that a gap is provided through an exterior surface of the neck section.

Figure 37:
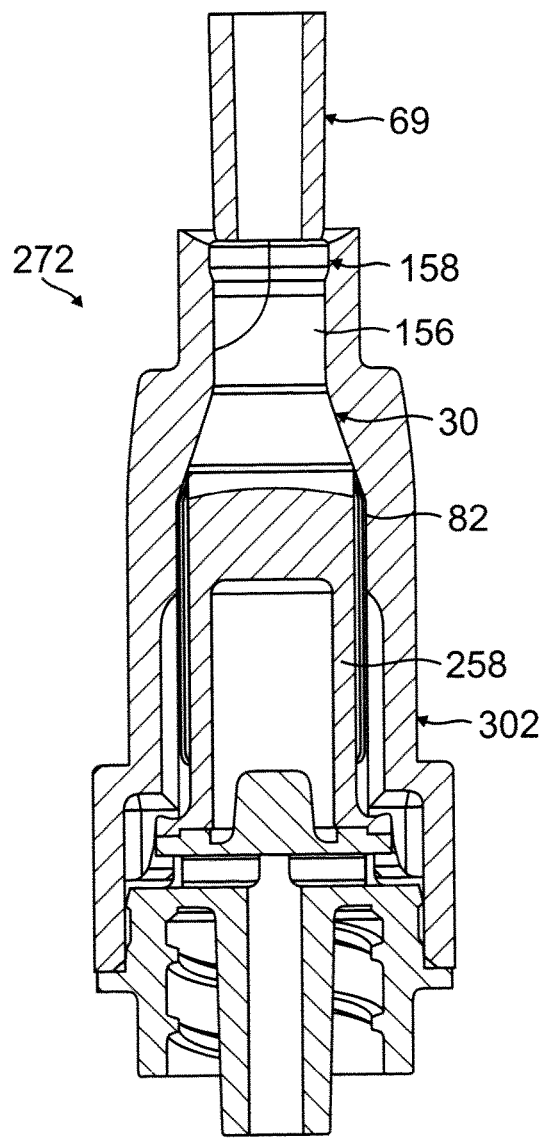
FIG. 37 is a simplified partial cross-sectional view of a valve including the piston of FIG. 34 in accordance with another embodiment of the present invention; *

In particular applications of the valve assembly having the preferred piston 258 of the present embodiment, a combination translational and rotational force is applied by the tip 69 of a syringe on the piston. This is generally the case, for example, if the syringe has a threaded collar configured for threaded engagement with the inlet of the valve assembly in a Luer lock arrangement Since the slit 260 is cut as a helix, the piston neck sections 268a and 268b react to the tip 69 by "twisting" or rotating about the longitudinal axis of the piston. The twisting action causes the sections 268a and 268b to rotate about the screw axis relative to each other in the enlarged lower section 82 of the valve housing (FIG. 37). As the piston neck sections 268a and 268b twist, they move in opposite directions relative to each other causing the slit 260 to diverge and the gap to widen at the upper slit section 262. The separation creates a gap 66 at the upper slit section 262, which extends across the top surface 162. The gap 66 forms a fluid pathway for fluid flow from either the tip 69 through the valve or towards the tip, if a sample was to be taken through the valve assembly 272. Concurrently, under the compression load of the tip 69, the pliable and resilient base 146 starts to buckle and contort. Thus, the piston 258 is understood to have a helical cut along an orientation such that when the syringe is threaded to the valve housing and the tip 69 imparts a combination rotational and translational force on the piston, the slit opens or widens. Conversely, when the syringe is removed from the valve housing, the reverse rotation of the syringe causes the slit to close to form a fluid tight seal, which is further facilitated by the geometry of the housing inlet relative to the upper neck section of the piston.

Figure 36:
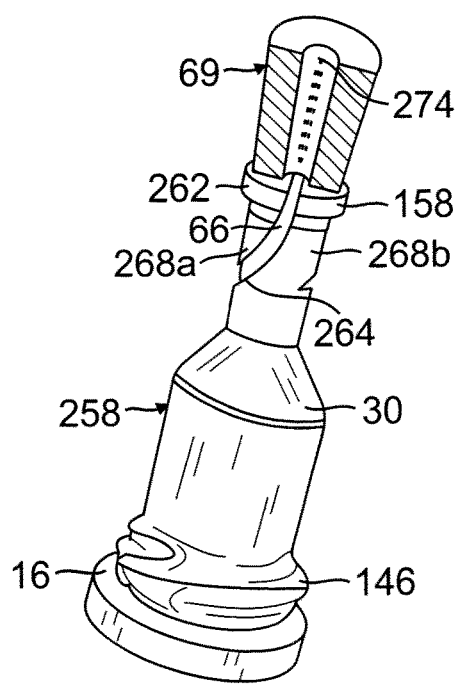
FIG. 36 is a semi-schematic partial cross-sectional partial perspective view of the piston of FIG. 34 moved to a second position by a tip of a medical implement.

FIG. 36 is a semi-schematic perspective view of the valve assembly 272 of FIG. 35 in a second position, which shows the tip 69 of the medical implement in a completely inserted position in the inlet nozzle of the valve housing. The tip 69 is stopped in the second position from being further advanced by the relative geometry of the tip 69 and the inlet nozzle of the valve housing. As the upper and lower neck sections 268a and 268b continue to twist away from each other, the gap 66 at the upper slit section 262 is further widen and the gap at the lower slit sections 264 widen. The pliable and resilient base 146 is further compressed and the random folds become more pronounced. Fluid flow from the medical implement may now flow through the lumen 274 defined by the tip 69, through the gap 66 and through the flow space defined by the exterior surface of the piston and the interior surface of the valve housing. The flow continues until it flows out of the outlet nozzle of the valve housing.

Upon removal of the tip 69 from the inlet nozzle of the valve housing, the pliable and resilient piston base 146 recoils and returns to its less compressed position The recoil acts to push the neck section 156 proximally towards the opening of the inlet nozzle. As the axial compression on neck section 156 is removed, the piston neck sections 268a and 268b begin to "untwist" due to the resiliency of the piston and the counter-rotation of the syringe tip. The neck sections 268a and 268b untwist until they return to their original position. The internal surfaces of the slit remain pushed together due to the restriction or smaller internal circumference of the inlet nozzle near the opening of the valve housing, which acts to hold the gap 66 closed and terminate fluid communication from between the inlet and the outlet of the invisible valve housing. It should be understood, that although a circumferential force is used to help hold the gap 66 closed, the internal surfaces of the slit remain in contact until forced to open by application of the axial compression of the neck section.

Figure 38:
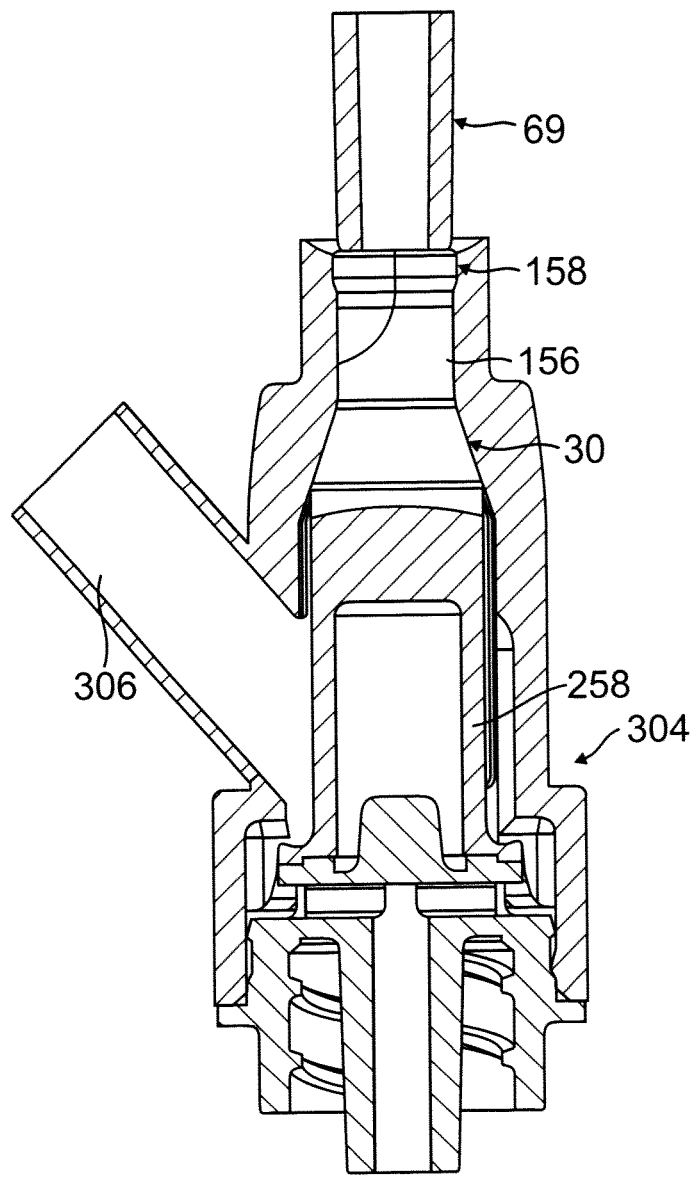
FIG. 38 is a simplified partial cross-sectional view of a Y-site valve including the piston of FIG. 34 in accordance with another embodiment of the present invention.

In one embodiment, piston 258 may be used in a Y-site valve housing 304 as shown in FIG. 38. In the Y-site valve housing 304, a secondary inlet 306 is formed in the housing. The secondary inlet 306 is formed in a separate leg of the housing 304 than that which is used to house the piston 258. The housing 302 may be molded as one monolithic part with two legs, as shown, or it may be made from different parts that are then solvent welded together or otherwise joined using well known techniques.

In a yet further aspect of the present invention, the piston 258 may be impregnated, coated, or both with an antimicrobial agent as described in Ser. No. 11/942,163, filed Nov. 19, 2007, which was previously incorporated herein by reference. Alternatively or in addition thereto, the valve housing for housing the piston may also be impregnated or coated with an antimicrobial agent.

Although limited embodiments of the needleless access valve assemblies and their components have been specifically described and illustrated herein, many modifications and variations will be apparent to those skilled in the art. For example, the various valves may incorporate luer-slips rather than luer threads, the medical implement may include a luer lock, the materials selected could be opaque or semi-opaque, different colors may be used, the dimensions can vary, etc. Furthermore, it is understood and contemplated that features specifically discussed for one valve embodiment may be adopted for inclusion with another valve embodiment, provided the functions are compatible. For example, certain curvatures and contours incorporated in one valve may be incorporated in another valve for aesthetic appeal and improved functionality, such as for improved gripping purposes. Accordingly, it is to be understood that the valve assemblies and their components constructed according to principles of this invention may be embodied other than as specifically described herein. The invention is also defined in the following claims.

What is claimed is:

1. A valve assembly comprising:
a valve housing having an interior cavity, a bottom opening, and an inlet nozzle having an inlet opening and an interior wall surface along a central axis;
a piston positioned inside the valve housing having a flange, a neck section, a body section, and a base; the piston further comprising a slit having a first slit surface and a second slit surface extending radially across two opposed exterior surface sections of the flange and lengthwise in a direction of the inlet opening towards the bottom opening and through at least part of the neck section below the flange, the first slit surface and second slit surface extending through at least part of the neck section below the flange and comprises an angle about the central axis.

2. The valve assembly of claim 1, wherein the slit extending through at an angle comprises a helical pattern configuration.

3. The valve assembly of claim 1, wherein the first slit surface and the second slit surface move from a first position wherein the surfaces are in contact to a second position in which a gap is formed between the surfaces.

4. The valve assembly of claim 3, wherein a portion of the body section buckles when the piston moves from the first position to the second position.

5. The valve assembly of claim 3, wherein the first slit surface and the second slit surface rotate in opposite directions about the central axis when moving from the first position to the second position.

6. The valve assembly of claim 1, wherein the flange is in contact with the interior wall surface of the inlet nozzle to force at least a portion of the first and the second slit surfaces into contact with one another.

7. The valve assembly of claim 1, wherein an antimicrobial agent is formed on at least one of the piston and the valve housing.

8. The valve assembly of claim 1, further comprising a plurality of threads disposed at the inlet nozzle of the valve housing.

9. The valve assembly of claim 1, wherein the valve housing comprises a second inlet opening.

10. A valve assembly comprising:
a piston positioned inside a valve housing, the piston comprising a flange, a neck section a body section comprising an upper section and a lower section defining an interior cavity, an exterior wall surface, and a base:
the valve housing comprising an inlet nozzle having an inlet opening, a body section defining an interior cavity having an interior wall surface, and a bottom opening;
wherein the neck section of the piston comprises a slit formed across the entire flange and through at least part of the neck section to the exterior wall surface of the piston in a helical configuration; the slit defining a fluid space with the interior wall surface of the valve housing for fluid flow through the inlet nozzle and out the bottom opening.

11. The valve assembly of claim 10, wherein the helical configuration of the slit comprises a rotation of the slit at an angle about a central axis of the piston.

12. The valve assembly of claim 10, wherein the helical configuration of the slit comprises two cut leading edges that point in a direction opposite to one another.

13. The valve assembly of claim 10, wherein the valve housing comprises a Y-site valve housing.

14. The valve assembly of claim 10, wherein at least one of the piston and the valve housing comprises an antimicrobial composition.

15. The valve assembly of claim 10, wherein the slit comprises a first slit surface and a second slit surface which move from a first position wherein the surfaces are in contact to a second position in which a gap is formed between the surfaces to form part of the fluid space.

16. The valve assembly of claim 15, wherein the first slit surface and the second slit surface rotate in opposite directions about the central axis when moving from the first position to the second position.

17. The valve assembly of claim 15, wherein a portion of the body section buckles when the piston moves form the first position to the second position.

18. A method of making a piston for use in an access port valve, said method comprising:
molding a piston, said piston comprising a neck section of reduced diameter compared to a body section, which defines an interior cavity; and
cutting a slit in the neck section;
wherein the cutting step comprises rotating a blade by an angle about an axis of the piston while translating the blade by a distance along the axis.

19. The method of claim 18, wherein the piston comprises an antimicrobial composition.

20. The method of claim 18, wherein the slit comprises a helically shaped configuration.

* * * * *

UNITED STATES PATENT AND TRADEMARK OFFICE
CERTIFICATE OF CORRECTION

PATENT NO. : 9,695,953 B2
APPLICATION NO. : 12/510937
DATED : July 4, 2017
INVENTOR(S) : Burnard et al.

Page 1 of 1

It is certified that error appears in the above-identified patent and that said Letters Patent is hereby corrected as shown below:

On the page 2, in Column 2, under "Other Publications", Line 15, delete "039849." and insert -- 039849, --, therefor.

In Column 4, Line 43, delete "invention; *" and insert -- invention; --, therefor.

In Column 5, Line 1, delete "herein" and insert -- herein, --, therefor.

In Column 6, Line 1, delete "spring" and insert -- spring. --, therefor.

In Column 8, Line 59, delete "valve," and insert -- valve. --, therefor.

In Column 9, Line 66, delete "alterative" and insert -- alternative --, therefor.

In Column 10, Line 64, delete "form" and insert -- from --, therefor.

In Column 18, Line 13, delete "arrangement" and insert -- arrangement. --, therefor.

In Column 18, Line 57, delete "position" and insert -- position. --, therefor.

In Column 20, Line 22, in Claim 10, after "a neck" delete "section" and insert -- section, --, therefor.

In Column 20, Line 25, in Claim 10, delete "base:" and insert -- base; --, therefor.

Signed and Sealed this
Twenty-sixth Day of February, 2019

Andrei Iancu
*Director of the United States Patent and Trademark Office*